United States Patent [19]
Ikeda

[11] Patent Number: 5,069,218
[45] Date of Patent: Dec. 3, 1991

[54] FETUS MONITORING APPARATUS

[75] Inventor: Makoto Ikeda, Fuji, Japan

[73] Assignee: Terumo Kabushiki Kaisha, Tokyo, Japan

[21] Appl. No.: 392,962

[22] PCT Filed: Feb. 3, 1988

[86] PCT No.: PCT/JP88/00099

§ 371 Date: Jul. 31, 1989

§ 102(e) Date: Jul. 31, 1989

[30] Foreign Application Priority Data

Feb. 3, 1987 [JP] Japan ............................. 62-14720
Feb. 3, 1987 [JP] Japan ............................. 62-14721
Feb. 3, 1987 [JP] Japan ............................. 62-22934
Feb. 3, 1987 [JP] Japan ............................. 62-22935

[51] Int. Cl.$^5$ ............................. A61B 5/02; A61B 8/02
[52] U.S. Cl. ............................. 128/670; 128/661.07
[58] Field of Search ......... 128/662.04, 661.07–661.10, 128/670

[56] References Cited

U.S. PATENT DOCUMENTS 3,703,168 11/1972 Frink .................................... 128/696
4,569,356 2/1986 Kyozuka .............................. 128/698

FOREIGN PATENT DOCUMENTS 48-36794 11/1973 Japan .
55-10985 1/1980 Japan .
56-29771 3/1981 Japan .
58-143735 8/1983 Japan .
60-85730 5/1985 Japan .
60-129903 8/1985 Japan .
61-13934 1/1986 Japan .
61-41442 2/1986 Japan .

Primary Examiner—Francis Jaworski
Attorney, Agent, or Firm—Frishauf, Holtz, Goodman & Woodward

[57] ABSTRACT

A fetus monitoring apparatus according to the present invention includes: a single chip signal processing processor for receiving a fetal heart signal and a mother labor pain intensity signal and for processing the heart beat signal to obtain a heart beat; a data processing processor for statistically processing a correlation between the mother labor pain intensity signal and the heart beat; a printing portion for recording the correlation obtained on a recording paper; an alarm portion for issuing an alarm in three stages including normal, caution and alarm on the basis of the fetal heart beat signal; a transmission portion for transmitting the labor pain intensity signal to another remote fetus monitoring apparatus; and a reception portion for receiving a labor pain intensity signal detected by another remote fetus monitoring apparatus.

5 Claims, 22 Drawing Sheets

| SUMMARY | | |
|---|---|---|
| NAME: | | AGE |
| | | PARA |
| DELIVERED | DATE/TIME: | |
| WEIGHT: g | MALE·FEMALE | WEEKS DAYS |
| APGAR: | (1 MIN) | (5 MIN) |
| START OF LABOR PAIN: | MONTH DAY HOUR MINUTE | |
| AMNIORRHEXIS: | MONTH DAY HOUR MINUTE | |
| | ARTIFICIAL · NATURAL | |
| COMPLICATION | | |
| COMMENT | | |
| | | 1986/12/24  13:20 |

Fig. 6

FETUS MONITORING APPARATUS

DESCRIPTION

1. Technical Field

The present invention relates to a fetus monitoring apparatus for monitoring a fetus in a mother together with the mother and a fetus monitoring system with this fetus monitoring apparatus incorporated therein.

2. Background Art

Suitable methods of supervising a fetus and a mother before and during labor include the monitoring of the fetal heart rate. This monitoring of the fetal heart rate is non-invasive, and enables observation of fetal activity in realtime.

The method of detection of the fetal heart rate employed in the monitoring of a fetus is roughly classified into two types: one, an external measurement and the other, an internal measurement. The outer measurements include (1) fetal phonocardiography, (2) ultrasonic Doppler method, and (3) mother abdomen induced fetal electrocardiography. The internal measurements include infant head induced fetal electrocardiography.

Among these methods, it is the ultrasonic Doppler method which ensures the most effective detection of the fetal heart rate during the NST (non stress test). The second best detection method is the fetal phonocardiography, with the mother abdomen induced fetal electrocardiography being the worst. In the infant head induced fetal electrocardiography, which is the internal measurement, spiral shaped electrodes have to be directly attached to the head of the infant. So, this method can be used only after the amniorrhexis or a rupture of membranes: it cannot be used before delivery. Thus, monitoring of the fetal heart rate which employs any of the external measurements is most useful for fetal observation which is conducted during the NST, because it allows fetal activity to be detected non invasively in realtime.

Generally, the requirements of the fetal monitoring apparatus are as follows:

I: It must be portable.

II: Since both the fetus and the mother have to be observed, it permits an observer to grasp the present conditions at a glance. At the same time, detailed data can be extracted whenever required.

III: It can also be utilized to monitor the twin that occurs occasionally.

IV: An alarm may be issued to draw the observer's attention and thereby help him determine fetal activity when the fetal heart rate exceeds a certain value. It is capable of issuing various types of alarms, depending on the present conditions of the mother and the fetus.

Next, how the conventional fetal monitoring apparatus fulfills the above described requirements, together with its shortcomings or problems, will be described below.

Items I and II

The recording system employed in most of the conventional fetal monitoring apparatus is of an analog type, such as a pen, which is capable of drawing only curves. Only a few of the conventional fetal monitoring apparatuses (e.g., the model 115 manufactured by Corometrics Medical Systems, Inc. (American Home Products)) employs a digital recording system, such as a thermal head, which is capable of recording data using characters. However, such a digital recording system is capable of recording only variations in the heart rate with time. Since a sufficient degree of density cannot be ensured in the recording of data using curves, batch processing may be performed on the variations in the heart rate when fetal activity is to be recorded. However, if batch-processing is performed on the variations in the heart rate after an emergency has arisen on the fetus or the mother, it may take too much time. Hence, during childbirth, a nurse or the like may periodically record the fetal heart rate, the period of labor pains, the time duration of uterine contractions and so on in graphs for fetal monitoring. Also, the mean heart rate may be obtained by looking at the fetal heart rate curve recorded by a pen or the like, if necessary.

It takes about 60 minutes to perform the NST. In the NST, data is recorded at a rate of 3 cm/min. A sheet of recording paper is fed at a rate of 1.8 m to 1.5 cm/min. It has a length of about 0.9 m. It is therefore a very troublesome task to read such a long sheet of recording paper and examine the overall data to observe the time differences between the event marks and the peaks or valleys of the fetal heart rate curve and the relationships between the time differences and the heights of these peaks or the depths of these valleys and thereby obtain one's view on the results of the NST. Such views may differ, depending on the individual.

Thus, although there is an enormous amount of data that can be used for determination, processing of the data is left to the individual's care. Furthermore, it may be impossible to process such a large amount of data, when necessary. These defects are thought to be caused by the following problems.

Conventionally, a large-scale apparatus is required to obtain accurate data on the heart rate from a heart beat signal. The conventional fetus monitoring apparatus is therefore used to record only the variations in the heart rate with time, and it is thus impossible to process the data obtained on the heart rate and so on in a form in which the information required for fetus monitoring can be obtained at a glance.

Item III

Although the frequency of occurrence of twins is low, it may cause serious problems. A primitive way of monitoring twins is to monitor them, one at a time, each for 10 minutes to 30 minutes, by using the Doppler probe of one fetus monitoring apparatus. This is because a fetus generally repeats awakening and sleeping cyclically in a period of about 20 minutes. Once the delivery starts, the period of time during which either of the twins is observed is shortened. In this method, while either of the twins is being monitored, the other cannot be observed, and this results in insufficient monitoring and hence unsatisfactory diagnosis.

Another method of monitoring twins employs two fetus monitoring apparatuses manufactured by different makers, i.e., the Doppler probes employing different frequencies. However, in this method, whereas one of the fetus monitoring apparatuses records both the fetal heart rate curve and the labor pain curve at the same time, only the fetal heart rate curve is recorded in the other apparatus. This is because the area of the abdomen is physically limited, thereby limiting the number of probes that can be attached to the mother and making it impossible for the labor pain curve to be obtained in the other apparatus. Thus, this method is also unsatisfactory.

In order to overcome the above-described inconveniences, attempts have been made to monitor the twins by utilizing the heart rate curve obtained by one ultrasonic Doppler fetus monitoring apparatus and the mother abdomen induced fetal electrocardiogram or the infant head induced fetal electrocardiogram, as well as the labor pain curve (e.g., YHP 8040A manufactured by HEWLETT-PACKARD). In that case, the mother abdomen induced fetal electrocardiogram or the infant head induced fetal electrocardiogram may be replaced by the heart rate curve obtained by the infant head fetal electrocardiography. However, in this method, the two fetal heart rate curves are recorded on the same sheet of recording paper with the labor pain curve of the mother being recorded on another sheet of paper, making this method an inconvenient one. Furthermore, mother abdomen induced fetal electrocardiographic waves may be superimposed on mother's electrocardiographic waves, deteriorating the signal to-noise ratio. Also, there is a limitation to the use of infant head induced electrocardiography, as stated above.

Item IV

In the conventional fetus monitoring apparatus, the state to be observed is divided into a normal state and an abnormal state, and an alarm is issued, indicating an abnormal state. In that case, when a threshold at which an abnormal state is observed is set at a low value, an alarm error often occurs, disturbing the observer by the sound of the alarm. On the other hand, with a high threshold, an alarm may not be issued in the abnormal state, preventing the apparatus performing its originally designed functions.

Generally, the fetus monitoring apparatus issues an alarm when the fetal heart rate reduces to 100 BPM (which means that the fetus is getting at fetal hyperbradycardia, which is one of the symptoms of fetal asphyxia) or less or when it increases to 180 BPM or above. However, a sudden alarm without warning may upset a doctor or the like, because in such a state, a fetus is already in a critical condition. Conventionally, a doctor who is upset turns up the heart beat volume (provided on the front surface of the monitoring apparatus) to monitor the activity of the fetus. However, monitoring of the fetus who has fallen into a critical condition doesnot reveal how that serious condition has developed. Also, it does not clarify the cause.

SUMMARY

Disclosure of Invention

In view of the aforementioned problems of the conventional fetus monitoring apparatus, an object of the present invention is to provide a fetus monitoring apparatus which can be very useful and which is capable of monitoring a fetus and a mother adequately. To this end, the present invention provides a portable fetus monitoring apparatus which comprises an input means for inputting a Doppler heart beat signal representative of heart beats at short sampling time intervals and converting the same into digital data, a memory means with programs therein, the programs being created to process the digital data representative of the Doppler heart beat signal using autocorrelation function and thereby calculate a periodic component of the Doppler heart beat signal to operate a heart rate from the periodic component, a single chip signal processing processor for performing logical operations in accordance with the programs and outputting the resultant heart rate, and a data processing processor which is separate from the signal processing processor, the data processing processor processing the heart rate output to produce fetal monitoring information.

In the fetus monitoring apparatus according to the present invention, a digital signal processing processor processes digital data representative of the Doppler heart beat signal in accordance with the programs stored in the memory means to calculate the periodic component of the Doppler heart beat signal and thereby operate the heart rate from the periodic component. In consequence, a Doppler heart beat signal can be processed at a high speed to obtain a heart rate. Furthermore, a data processing processor for processing the obtained data on the heart rate is provided separately from the signal processing processor. This enables the above-described signal processing and the data processing required to visually record the desired information on the fetus and mother to be performed parallel to each other. Because of this parallel processing and the provision of a single chip signal processing processor, the overall size of the apparatus can be reduced.

The present invention further provides a fetus monitoring apparatus which is useful and which is capable of monitoring a fetus and a mother adequately. This fetus monitoring apparatus comprises an input means for inputting a Doppler heart beat signal representative of fetal heart beats and converting the same into digital data, a memory means for storing the Doppler heart beat signal in the order input, a feature extraction means for extracting a feature of the Doppler heart beat signal stored in the heart beat memory means, and a recording means for recording data representing the feature of the Doppler heart beat signal.

In the fetus monitoring apparatus arranged in the manner described above, the feature of the information on the fetus can be extracted from the Doppler signal stored in the order input, and the extracted feature can be recorded.

The present invention further provides a fetus monitoring apparatus which is useful and which is capable of monitoring a fetus and a mother adequately. This fetus monitoring apparatus comprises an input means for inputting a mother temperature signal and converting the same into digital data, a memory means for storing the mother temperature signal in the order input, a feature extraction means for extracting a feature of the mother temperature signal stored in the memory means, and a recording means for recording data representative of the feature of the mother temperature signal.

In the fetus monitoring apparatus arranged in the manner described above, the feature of the mother temperature signal stored in the order input can be extracted, the extracted feature being recorded.

The present invention further provides a fetus monitoring apparatus which is convenient to use and which is capable of monitoring a fetus and a mother adequately. This fetus monitoring apparatus comprises a first memory means for storing a fetal state signal representative of a fetal state in the order input, a first feature extraction means for extracting changes in a feature of the fetal state signal stored in the first memory means, a second memory means for storing a mother state signal representing the state of a mother in the order input, a second feature extraction means for extracting changes in a feature of the mother state signal stored in the second memory means, an operation means for operating the fetal state signal and the mother state signal which have been stored as well as a time difference between the occurrence of the changes in the feature of the fetal state signal and the occurrence of the changes in the feature of the mother state signal which have been extracted, and a recording means for visually and two-dimensionally recording a correlation between the time difference and the changes in the feature of the fetal state signal.

In the fetus monitoring apparatus arranged in the manner described above, the correlation between the fetal state and the mother state can be recorded over a long period of time in the form in which it can be seen at a glance.

The present invention further provides a fetus monitoring apparatus which is convenient to use, which is capable of monitoring a fetus and a mother adequately, and which is used in a multiple fetuses monitoring system as one component thereof. This fetus monitoring apparatus comprises a mother signal detection means for detecting a mother signal representative of the state of a mother, a first interface means for transmitting the mother signal to another fetus monitoring apparatus, a second interface means for receiving a mother signal from another fetus monitoring, a Doppler probe employing a different frequency for each fetus, a Doppler heart beat signal input means for inputting a fetal Doppler heart beat signal from the Doppler probe, at least a data processing means for correspondingly processing the mother signal received by the second interface means and the Doppler heart beat signal input by the Doppler heart beat signal input means, and a recording means for recording the two signals which have been processed.

The fetus monitoring apparatus arranged in the manner described above is normally used to monitor a single fetus. In the case of monitoring multiple fetuses, the Doppler heart beat signal input means of a plurality of fetus monitoring apparatuses are set for the individual fetuses, and the mother state signal which is input to the mother state signal input means of one of the fetus monitoring apparatuses is transmitted to other fetus monitoring apparatuses. In consequence, the fetus monitoring apparatus is normally used for monitoring a single fetus. It can be combined with other apparatuses to monitor multiple fetuses, particularly, twins. This improves cost performance The present invention further provides a multiple fetuses monitoring system which is convenient to use, which is capable of monitoring a fetus and a mother adequately, and which incorporates at least two fetus monitoring apparatuses. A first fetus monitoring apparatus includes a mother signal detecting means for detecting a mother signal representative of the state of a mother, a first interface means for transmitting the mother signal to a second fetus monitoring apparatus, a first Doppler probe employing a first frequency, a first Doppler heart beat signal input means for inputting a fetal Doppler heart beat signal from the Doppler probe, a first data processing means for correspondingly processing the mother signal detected and the Doppler heart beat signal input by the Doppler heart beat signal input means, and a first recording means for recording the two signals which have been processed. A second fetus monitoring apparatus includes a second interface for receiving the mother signal from the first fetus monitoring apparatus, a second Doppler probe employing a second frequency different from the first frequency, a second Doppler heart beat signal input means for inputting a fetal Doppler heart beat signal which is output from the second Doppler probe, a second data processing means for correspondingly processing the mother signal received by the second interface means and the Doppler heart beat signal input by the second Doppler heart beat signal input means, and a second recording means for recording the two signals which have been processed. The fetuses monitoring system according to the present invention incorporates at least one first fetus monitoring apparatus and at least one second fetus monitoring apparatus.

Thus, the second fetus monitoring apparatus does not incorporate a detection means for detecting a labor pain intensity signal, and this reduces the production cost of the second fetus monitoring apparatus and hence that of the overall multiple fetuses monitoring system.

The present invention further provides a fetus monitoring apparatus which is easy to use, which is capable of monitoring a fetus and a mother adequately, and which includes an alarm means for issuing an alarm in at least two stages. This fetus monitoring apparatus comprises an input means for inputting a signal representative of the state of a fetus, a means for comparing a value of the signal with a plurality of thresholds corresponding to the plurality of alarm stages, and an amplification means for amplifying the fetal state signal to a predetermined volume, the fetal state signal which has been amplified to the predetermined volume being input to the alarm means to allow one of the at least two types of alarms to be issued.

In the fetus monitoring apparatus arranged in the manner described above, since the alarm means issues a plurality of types of alarms corresponding to the plurality of types of thresholds, a suitable measure can be taken before the fetus falls into a serious condition. A fetal state sound, i.e., the fetal state signal, is output as an alarm sound. In consequence, a doctor who hears an alarm is informed of the fetal state.

In one form of the present invention, the fetal state signal is output an alarm sound in an alarm indicating caution. fetus, a means for comparing a value of the signal with a plurality of thresholds, and an alarm means for issuing a plurality of types of alarms corresponding to the plurality of types of thresholds. In the fetus monitoring apparatus arranged in the manner described above, since the alarm means issues a plurality of types of alarms corresponding to the plurality of types of thresholds, a suitable measure can be taken before the fetus falls into a serious condition.

BRIEF DESCRIPTION OF THE DRAWINGS

FIGS. 6 to 9 respectively show the formats of the fetus monitor diagrams which are output from the fetus monitoring apparatus of FIG. 1A;

DETAILED DESCRIPTION

An embodiment of the fetus monitoring apparatus according to the present invention will be described below with reference to the accompanying drawings.

External View of the Embodiment

Figure 1A:
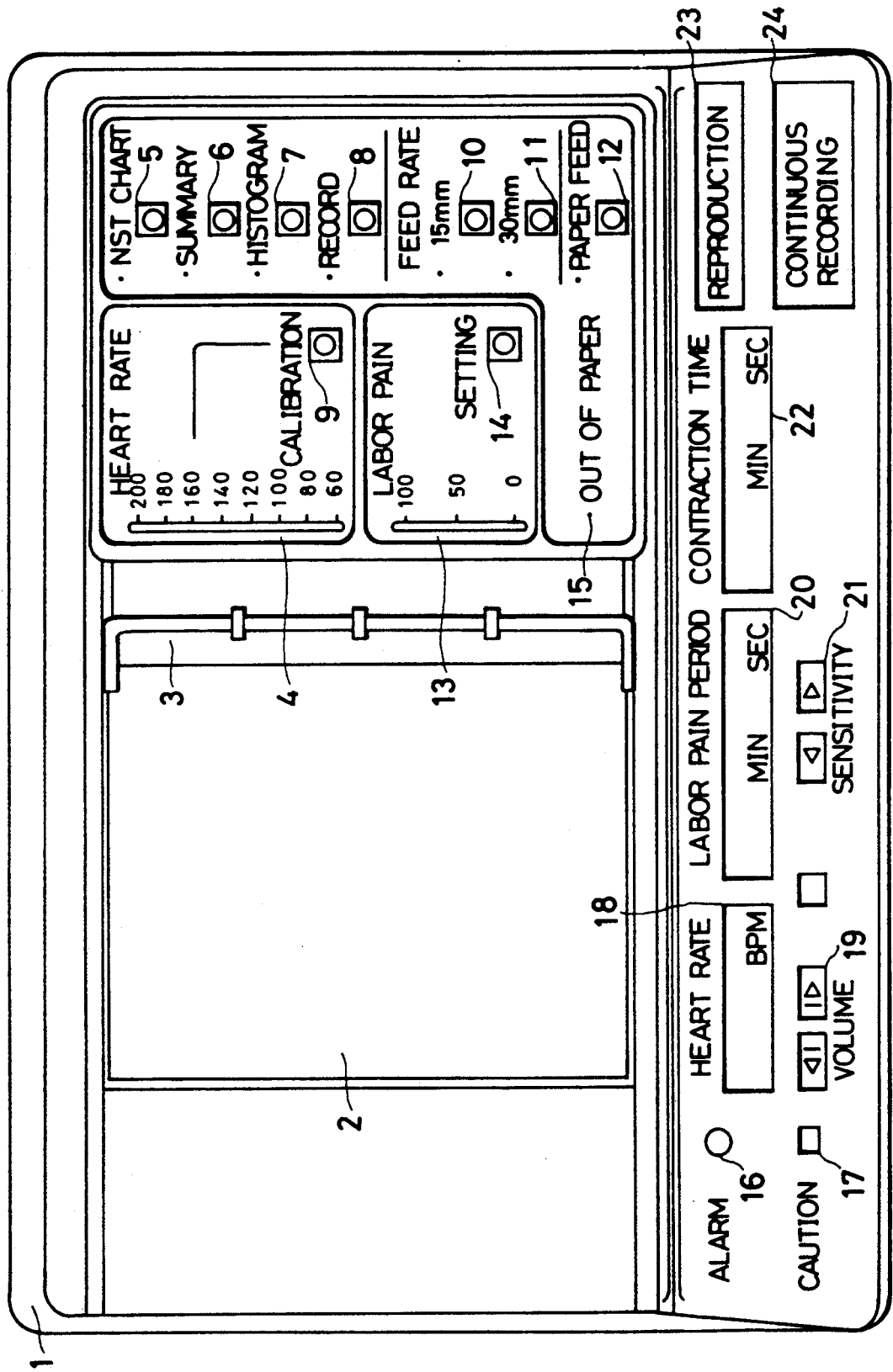
FIG 1A is a plan view of a fetus monitoring apparatus, showing an embodiment of the present invention.
Figure 1B:
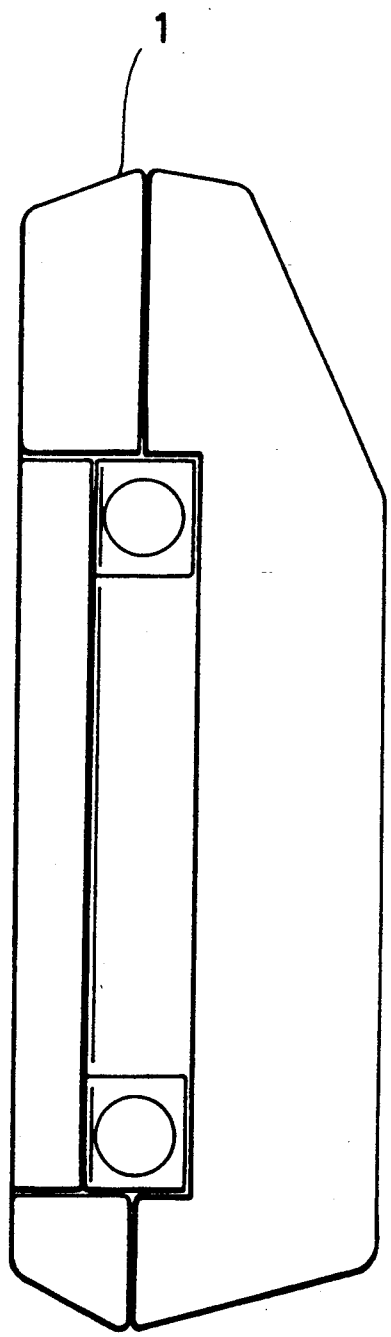
FIG. 1B is a side view of the fetus monitoring apparatus of FIG. 1A, as seen when looking from the right side as viewed in FIG. 1A.

FIGS. 1A and 1B are respectively plan and right side views of a fetus monitoring apparatus 1. Referring first to FIG. 1A, a reference numeral 3 denotes a printing unit with a thermal line head incorporated therein. A sheet of recording paper on which data has been printed by the printing unit 3 is fed along a base 2 from the right side to the left side as viewed in FIG. 1A. The sheet of recording paper is unrolled from a roll (not shown) within the fetus monitoring apparatus and is supplied to the printing unit 3.

A reference numeral 4 denotes an LED portion arranged in an array for displaying a fetal heart rate. A reference numeral 9 designates a calibration switch. Pressing of this calibration switch 9 starts calibration for the printing unit 3.

Reference numerals 5, 6, 7 and 8 denote switches to be pressed when four major functions of the fetus monitoring apparatus 1 are to be started The four major functions include that of outputting an NST graph, which is started by the pressing of the switch 5, that of outputting a summary, which is started by the pressing of the switch 6, that of outputting a heart rate histogram, which is started by pressing the switch 7, and that of outputting a record of the heart rate or the like, which is started by pressing the switch 8. These functions will be described later in detail.

Reference numerals 10 and 11 denote recording paper feed rate switch-over switches (the feed rates set in the switches are 15 mm/min and 30 mm/min, respectively). A reference numeral 12 designates a paper feed switch. Reference numerals 13, 14 and 15 respectively denote an LED portion arranged in an array for displaying a labor pain intensity, a switch for zero setting a labor pain intensity signal, and an LED portion for indicating that the recording paper is out.

An alarm LED 16 lights up when a fetus falls into an abnormal condition. A caution LED 17 lights up when a fetus needs a special care. In addition to these alarms made by the LEDs, although not shown in FIG. 1 (shown by a reference number 121 in FIG. 3A), a speaker by which fetal heart beats are made audible is provided on the bottom of the apparatus as an acoustic alarm. The volume of this speaker 121 is adjusted by a volume adjusting switch 19. Movement of this adjusting switch 19 varies the resistance of a volume 134 shown in FIG. 3. The volume of the speaker can be preset by means of a volume (indicated as a volume 133 in FIG. 3B) provided on the rear surface of the apparatus, although not shown in FIG. 1. Among the volumes of the speaker set by means of the two volumes (133 and 134), the larger one is given priority over the other when the alarming function is in operation.

The fetal heart rate is displayed by a 7-segment LED portion 18. The period of labor pains and the time duration of uterine contractions are respectively displayed by 7-segment LED portions 20 and 22. The sensitivity of a labor pain intensity signal detecting circuit (FIG. 5B) is adjusted by an adjusting switch 21. The sensitivity of the labor pain intensity signal detecting circuit is adjusted by varying the resistance of a VR176 shown in FIG. 5B.

Variations in the heart rate data and the labor pain intensity data stored in a buffer (corresponding to a RAM in a CPU 100 shown in FIG. 3B) of the present apparatus with time are output and recorded on a sheet of recording paper by the pressing of a reproduction switch 23. The reproduction function accomplished by the pressing of this switch 23 allows the data in the buffer to be recorded on a sheet of paper at an arbitrary time. In this fetus monitoring apparatus 1, storage of the heart rate and the labor pain intensity in the buffer starts without any specific operation, such as pressing of any special switch, conducted by an operator. There is a limitation to the capacity of the buffer (about 40 minutes at a maximum). In consequence, data stored in the buffer after the recording of data on the sheet of recording paper remains in the buffer for 40 minutes at a maximum. After 40 minutes has elapsed, the data which stays in the buffer is updated by new data.

The heart rate data or the labor pain intensity data which is being input to the apparatus at present is sequentially recorded on a sheet of recording paper by the pressing of a continuous recording switch 24.

Figure 2:
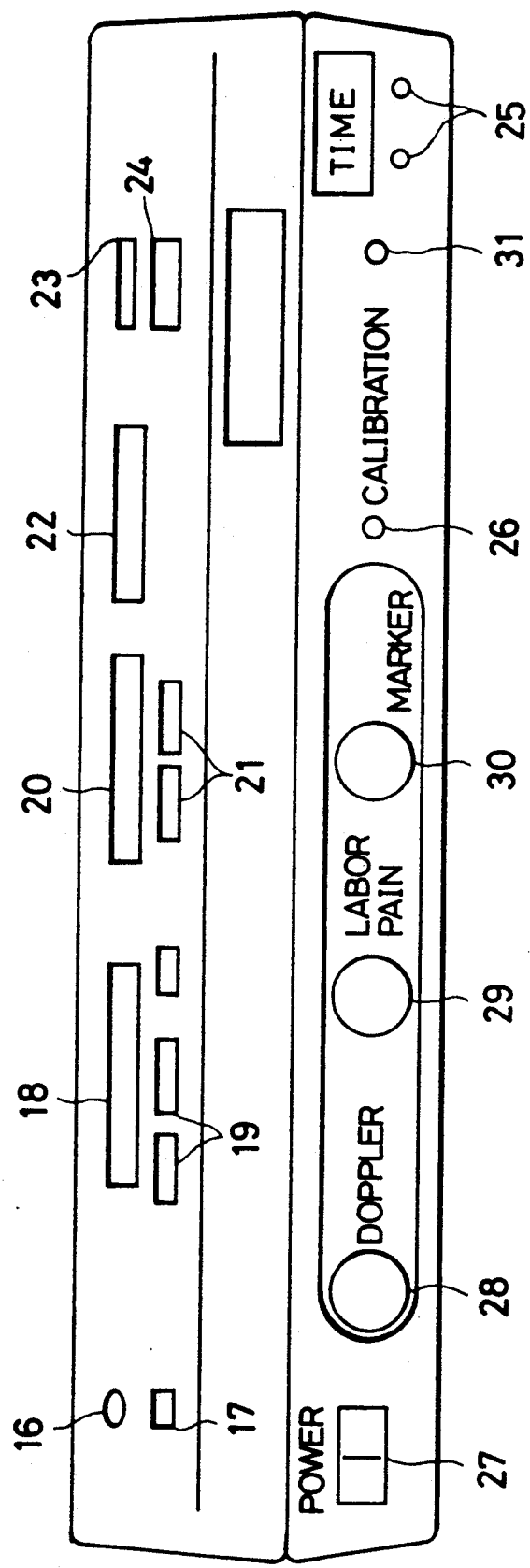
FIG. 2 is a front view of the fetus monitoring apparatus of FIG. 1A.

FIG. 2 is a front view of the fetus monitoring apparatus 1. A switch 25 is used to set the time. A reference numeral 26 denotes a volume for calibration. The calibration volume 26 is adjusted in such a way that it ensures that the printing unit 3 prints a straight line at a height representing 160 BPM while the reference heart beat signal representing 160 BPM is being generated by the pressing of the switch 8. The labor pain intensity is zero set by means of a volume 31.

A reference numeral 27 designates a power switch. Reference numerals 28, 29 and 30 respectively denote a heat beat Doppler signal input terminal, a labor pain intensity signal input terminal and an event marker signal input terminal.

Major Function of the Apparatus

Although schematically described previously, the major functions of the present apparatus will be described below in detail. They include:

(1): Summary (shown in FIG. 6) output function (started by the pressing of the switch 6), (2): NST graph (shown in FIG. 7) output function (started by the pressing of the switch 5), (3): Heart rate histogram (shown in FIG. 8) output function (started by the pressing of the switch 7), (4): Delivery record (shown in FIG. 9) output function (started by the pressing of the switch 8), (5): The present heart rate/labor pain intensity printing out function (started by the pressing of the switch 24), (6): Two-stage alarm function (performed by both sound and color), (7): Stored data reproduction function (started by the pressing of the switch 23), (8): Heart rate, the period of labor pains and the time duration of uterine contraction displaying function (performed by the LEDs 20 and 22)

(9): Data communication and data interface function with an external apparatus, which is particularly important for monitoring twins, (10): Intensified data processing function (done by a DSP 103). The provision of the data processing function listed in Item 10 enables other functions from (1) to (9)

It is also to be noted that the fetus monitoring apparatus according to the present invention also has the functions which are incorporated in the conventional monitoring apparatus, in addition to the above described functions from (1) to (10).

Circuit Configuration of This Embodiment

Figure 3A:
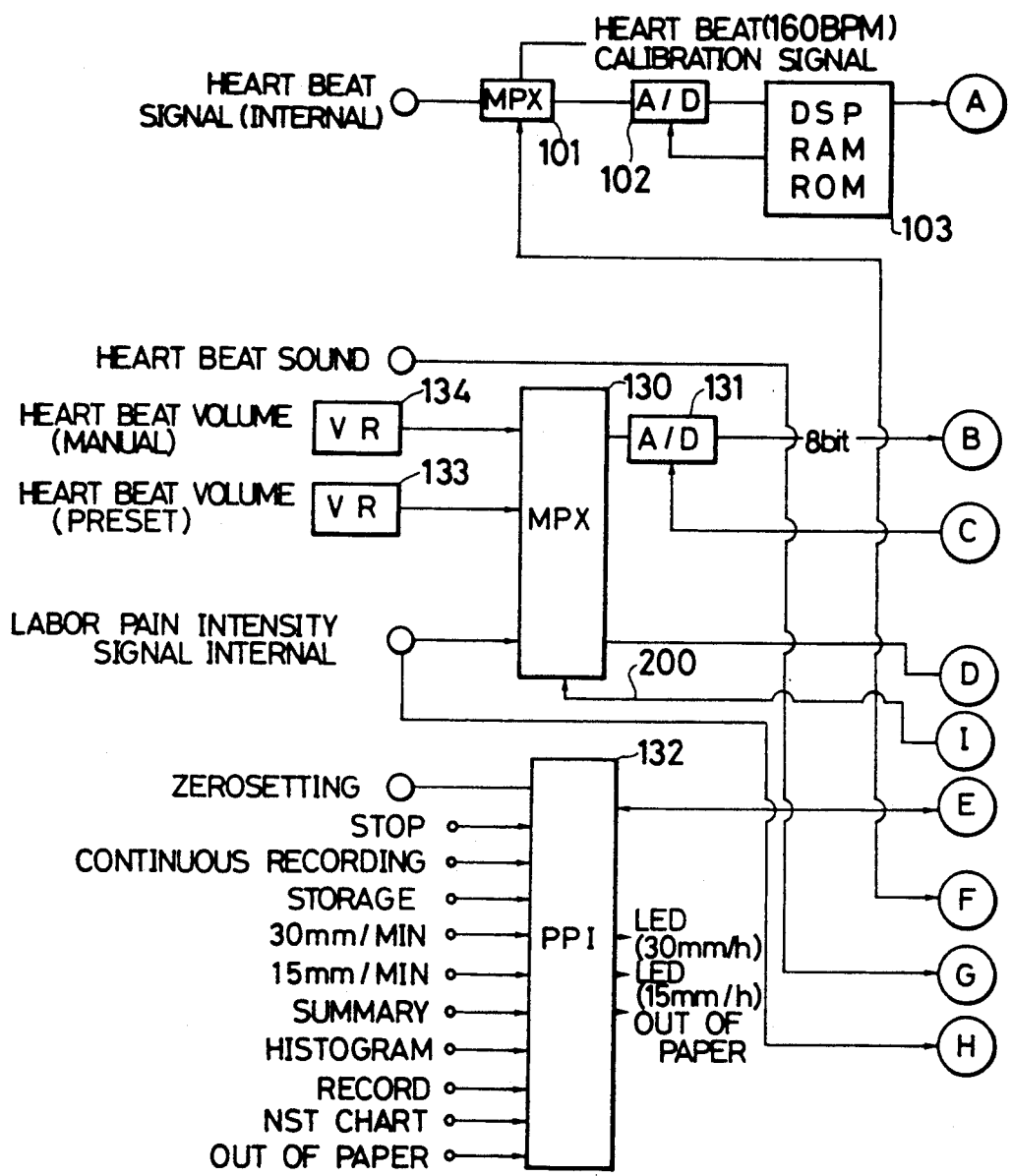
FIGS. 3A and 3B are circuit diagrams of a digital signal processing unit of the fetus monitoring apparatus of FIG. 1A.
Figure 3B:
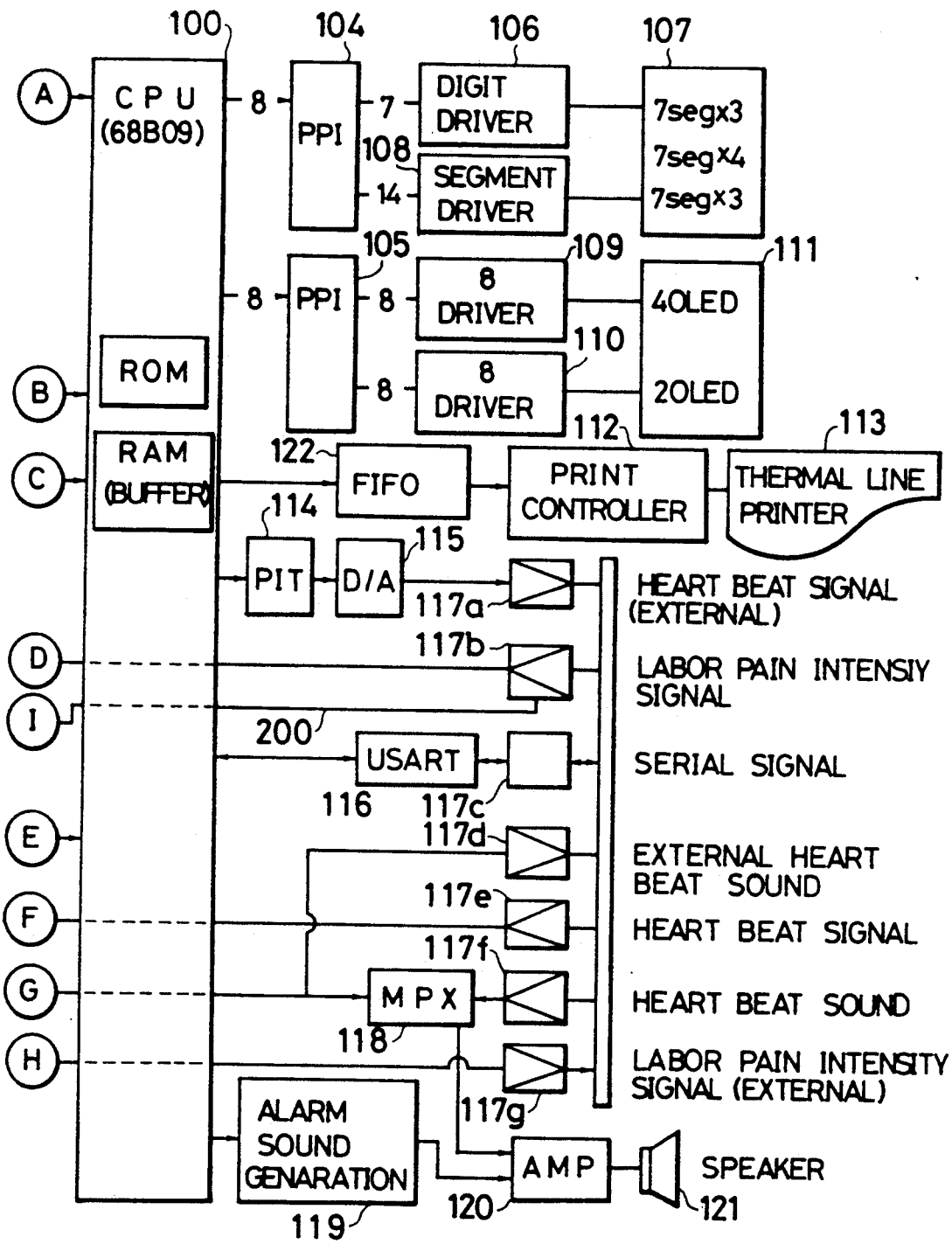
Figure 4:
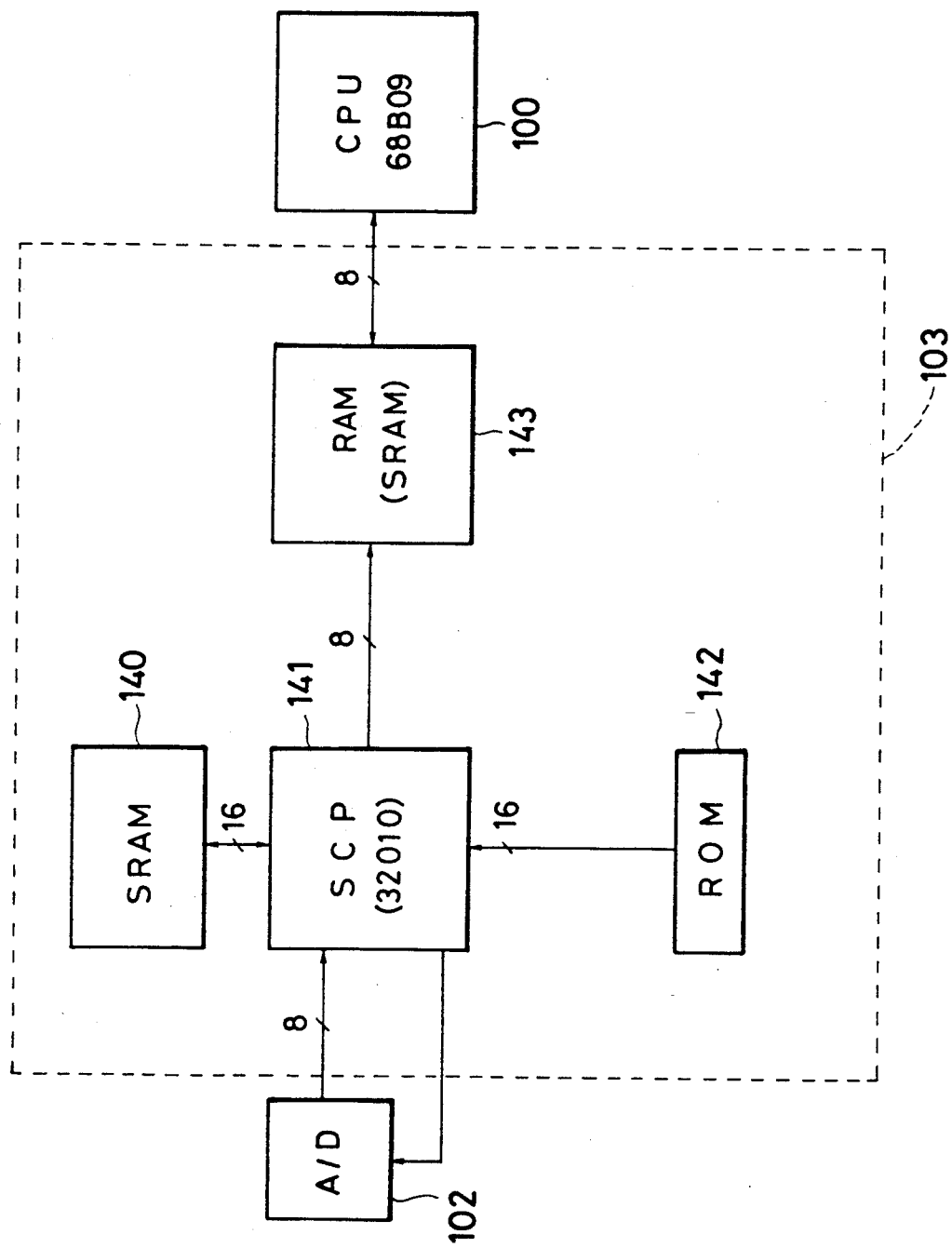
FIG. 4 is a circuit diagram of a digital signal processor (DSP)
Figure 5A:
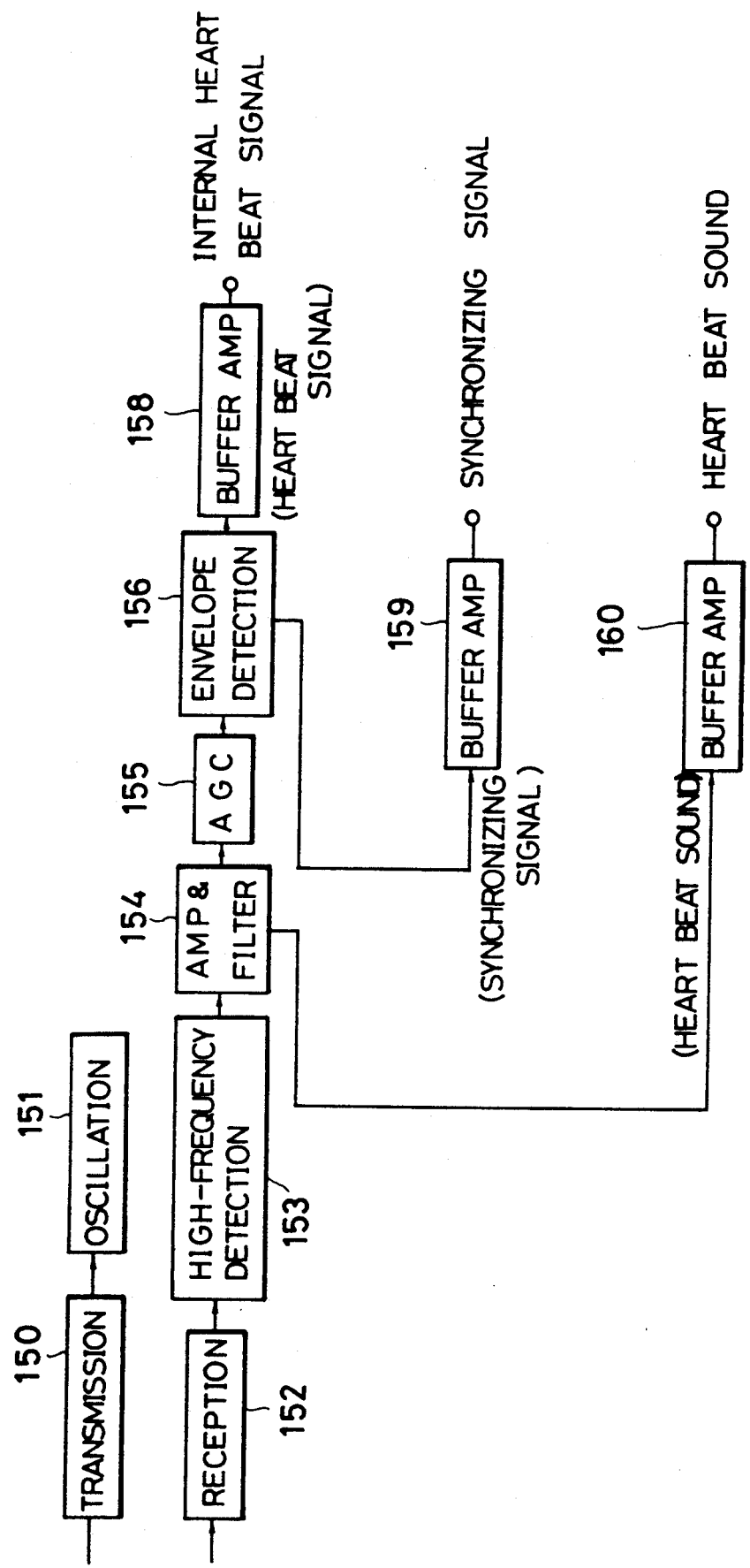
FIGS. 5A and 5B are circuit diagrams of analog signal processing circuits for respectively detecting a heart beat signal and a labor pain signal.
Figure 5B:
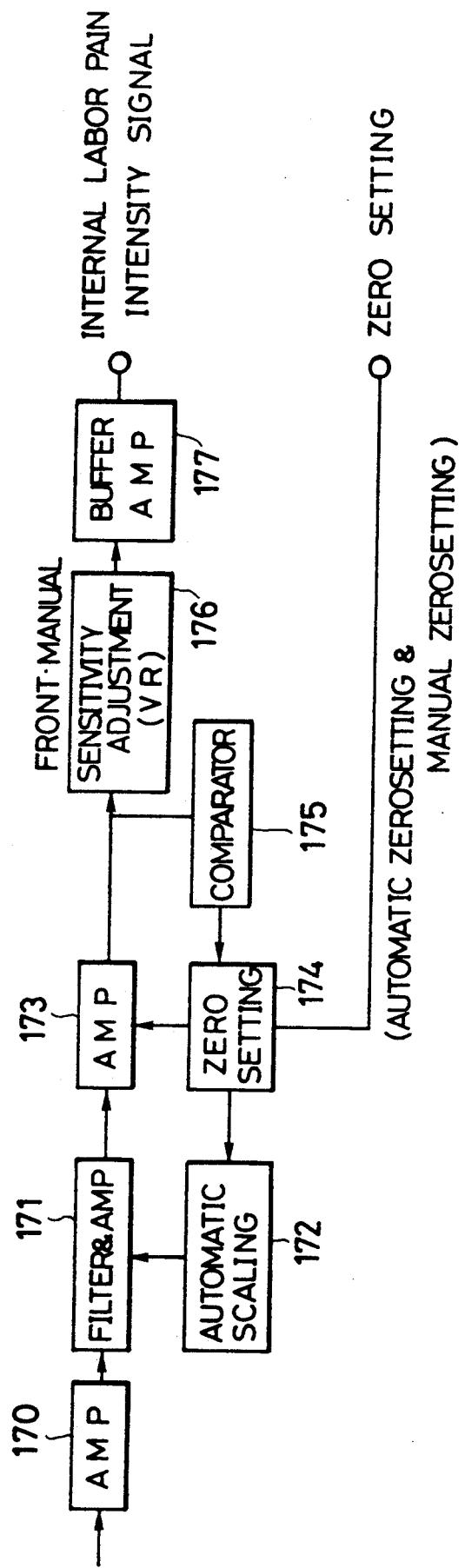

The configuration of the circuits required to execute the above-described functions will be described below with reference to FIGS. 3A to 5B. FIGS. 3A and 3B are circuit diagrams of a digital signal processing unit, FIG. 4 is a circuit diagram of a DSP 103 incorporated in the digital signal processing unit shown in FIG. 3A, and FIGS. 5A and 5B are circuit diagrams of an analog signal processing unit.

Analog Signal Processing Circuit

First, an analog circuit (shown in FIGS. 5A and 5B) will be described. FIG. 5A shows an analog signal processing circuit for measuring a heart rate using ultrasonic waves. The outputs of this circuit are an internal heart beat signal and a heart beat sound (no synchronizing signal is used in this embodiment). These two signals are input to a digital circuit shown in FIG. 3.

Ultrasonic waves are radiated toward a fetal heart from a transmission unit 150. The heart beat Doppler signal reflected by the heart is received by a reception unit 152, and a received signal is sequentially passed through a high-frequency detection circuit 153, an amplifier 154, an automatic gain control circuit 155, and an envelope detection circuit 156 where the envelope of the signal is detected to obtain an internal heart beat signal. Here, "internal" in the internal heart beat signal means that this signal is used "internally" within the apparatus. As will be explained later, a heart beat signal, called an external heart beat signal, is output from this first fetus monitoring apparatus 1 to a second monitoring apparatus. This external heart beat signal output to the second apparatus is used by the second apparatus to monitor a twin. The heart beat sound which has been amplified by the amplifier/filter 154 is output to a speaker (indicated by a reference numeral 121 in FIG. 3A) through a multiplexer 118. At the same time, the heart beat sound is output to an external apparatus through an output driver 117d as an external heart beat sound signal.

FIG. 5B shows a circuit used to obtain a labor pain intensity signal. The labor pain intensity is detected as a strain measured by a stress strain sensor worn around the abdomen of a gravida when she stops breathing. Such a stress-strain sensor is a known one, description thereof being omitted. Zerosetting of the labor pain intensity is performed by adjusting the sensitivity adjusting switch 21. Adjustment of the sensitivity adjusting switch 21 varies the resistance of a volume 176.

There are an "internal" labor pain intensity signal and an "external" labor pain intensity signal.

Thus, the three major signals which the fetus monitoring apparatus 1 produces are a heart beat signal, a heart beat sound signal and a labor pain intensity signal. There are internal and external signals in each of these three signals. In a case where the two apparatuses 1 are connected to each other, like a system shown in FIG. 11 in which a monitoring apparatus 200 is connected to a monitoring apparatus 201, the apparatus 200 discriminates the signal which it detects by itself from the signal which it receives from the apparatus 201 in the manner described below. Either the internal heart beat signal detected by the monitoring apparatus 200 or the external heart beat signal received from the monitoring apparatus 201 (through a receiver 117e) is selected by a multiplexer 101, the selected heart beat signal being converted to digital data by an A/D converter 102. The multiplexer 118 selects either the internal or external heart beat sound, as stated previously, the selected heart beat sound being amplified by an amplifier 120. The labor pain intensity signal is selected by a multiplexer 130, the selected one being converted to digital data by an A/D converter 131.

Digital Signal Processing

Digital signal processing is performed by the circuits shown in FIGS. 3A, 3B and 4.

The digital signal processing will be described in detail below with reference to FIG. 3. The circuit shown in FIG. 3 includes:

a main CPU 100 for controlling the entirety of the apparatus, a DSP (digital signal processor) 103 for detecting a heart rate from the internal heart beat signal, an A/D converter 102 for converting an internal labor pain intensity signal into digital data, a PPI (programmable peripheral interface) 132 into which the states of various types of switches are input, a PPI 104 used to drive the LED portions 18, 20 and 22, a PPI 105 used to drive the LED portions 4 and 13, a printer controller 112 for controlling a thermal printer 113, a FIFO (first in first out) buffer 122 for storing data corresponding to a maximum of 12 hours which is to be printed out in a delivery report, an NST graph and so on, an external interface consisting of transmission/reception circuits 117a to 117g and so on, a speaker 121 for making an audible alarm, and a PPI 124 used to drive an alarming LED 125.

The main CPU 100 incorporates a microprocessor 68B09 manufactured by an American semiconductor firm, Motorola, a 32 K byte RAM, a ROM with programs to be described later stored therein, and so on.

The LED display of the heart rate, the labor pain intensity, the uterine contraction time and so on is performed using a 7-segment LED portion 107. The heart rate and the labor pain intensity are also displayed in an analog way by an LED portion 111 in which the LEDs are aligned on a line. Display of the paper feed rate and that of no paper are performed by the PPI 132.

The CPU 100 periodically scans the MPX (multiplexer) 130 so as to select either the volume 133 or 134 and either an internal labor pain intensity signal or an external labor pain intensity signal, the selected ones being A/D converted by the A/D converter 131. The CPU 100 stores the resultant digital labor pain intensity signals in the internal buffer in the order in which they are detected by the apparatus.

The PPI 132 monitors the on/off state of the various switches, and interrupts the CPU 100 when it detects any change. Other circuit configurations will be described later in detail in connection with relevant functions.

Summary Function

Pressing of the switch 6 starts the printing out of the format shown in FIG. 6. A nurse or the like makes an entry of the name of a fetus or the like on the printed form.

NST Graph Output Function

Figure 7:
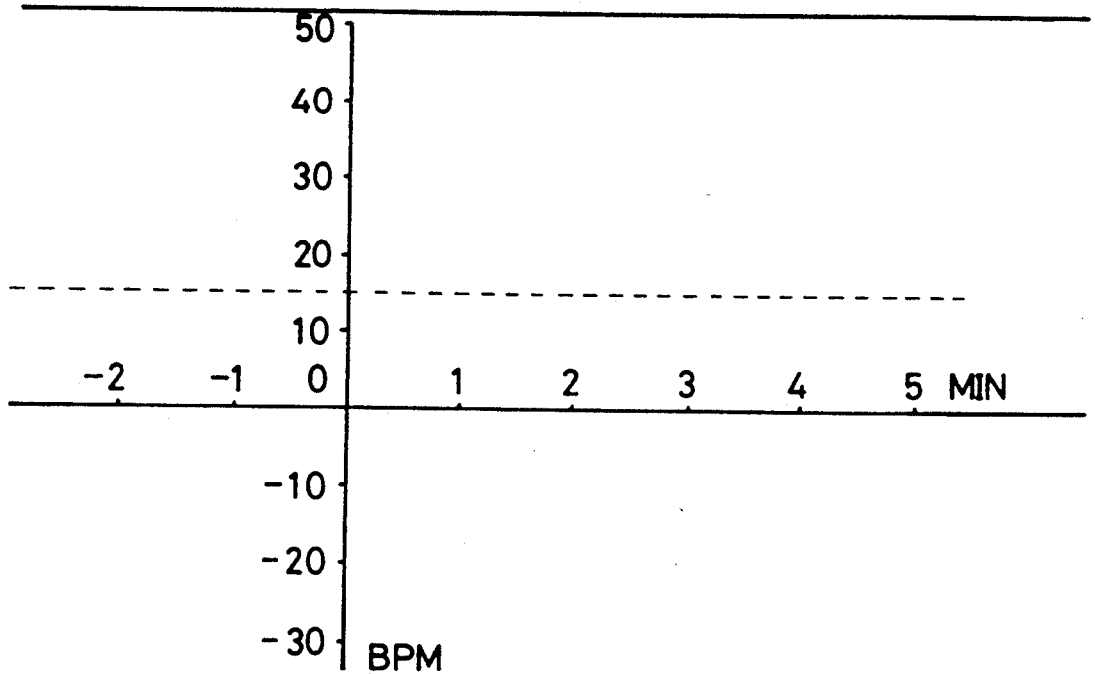

This function is started by the pressing of the switch 5. FIG. 7 shows the format of this NST graph. NST is performed for the following reasons. Examination of the fetal heart rate is an effective way of assessing fetal activity as well as high risks, such as fetal asphyxia, a suspected case of fetal asphyxia, latent fetal asphyxia (non-reactive), and fetal congenital disorders (which can be confirmed by ultrasonic diagnosis). One of the riseful tests for the fetal heart rate is an NST (non-stress test). In this test, the fetal heart rate, together with the fetal movements (recorded as event marks) or the natural uterine contractions, are physiologically examined without applying a stress such as drugs so as to estimate the well-being of the fetus. This NST is conducted on all pregnant women. It is capable of discriminating highly risky pregnancies. In this test, a gravida holds a switch in her hand and presses it each time she feels a fetal movement, by means of which an event mark signal corresponding to an event mark is input to a marker input terminal 30.

An NST can be conducted effectively when the pregnancy reaches between the twenty-fourth week and the thirty-seventh week. In may be said in this connection that the loss of an embryo from the uterus before the twenty-three week of pregnancy is a miscarriage, that expulsion of a viable infant from the twenty fourth week to the thirty sixth week of pregnancy is called premature labor, that labor taking place from the thirty-seventh week to the forty-first week of pregnancy is normal labor, and that labor occurring after the forty-first week of pregnancy is called postmature labor. It takes about 40 to 60 minutes to conduct an NST. This is because a fetus generally repeats awakening and sleeping cyclically about every 20 minutes. This is why data on the heart rate or the like should be stored in memory in apparatus 1 for 40 minutes at a minimun.

When the result of the NST is reactive (1) or when a nonreactive result changes to a reactive result (2), the NST will be continued at a frequency between once and twice per week. Similarly, when the result of the NST is nonreactive (3), the NST will be conducted at a rate of two per day. In a suspected case of fetal asphyxia, NST's will be repeatedly conducted to keep a close watch on the fetus. In the case of fetal asphyxia, a Cesarean operation will be performed. In the fetal management in a pregnancy, to extract the fetus safely is most essential. It is reckless to extract the fetus without checking whether or not the fetus has a risk factor. It is therefore important to start NST's several weeks before labor to examine fetal activity.

As stated previously, it takes about 60 minutes to complete one NST. In an NST, printing is performed at a rate of 3 cm/min and a sheet of recording paper is fed at a rate ranging from 1.8 m/min to 1.5 cm/min. The length of the recording paper generally reaches about 0.9 m. Conventionally, data printed on such a long sheet of recording paper is the only data that a doctor can obtain for diagnosis, as stated previously. As shown in FIG. 7, the NST graph employed in this embodiment is a graphic representation of such a data group, which is designed to eliminate the conventionally employed lengthy recording paper.

In this NST chart are shown the "time difference" between the occurrence of event marks and the occurrence of the peaks (or valleys) of a fetal heart rate curve, and the "heart rate difference" between the mean heart rate and the peaks of the fetal heart beat curve. These "time differences" and "heart beat differences" are extracted from the overall data stored in the buffer in the CPU 100, and are put into the form of a graph to illustrate the correlation (distribution) between them. In the graph, the axis of the abscissa represents the time difference, and the axis of the ordinate represents the heart beat difference.

Figure 10A:
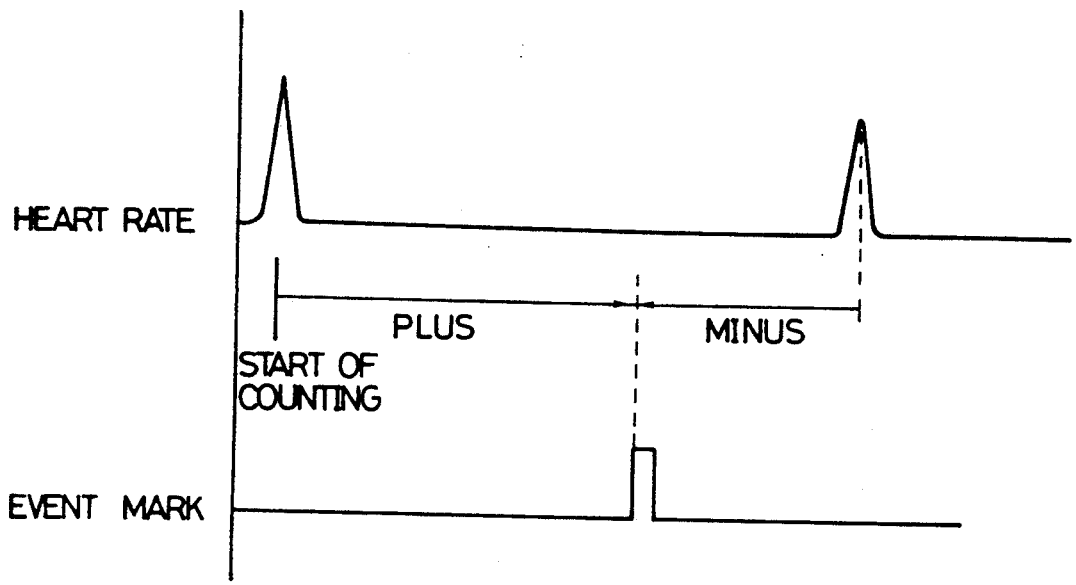
FIGS. 10A and 10B illustrate the algorithm used to obtain the time difference in the non stress test.
Figure 10B:
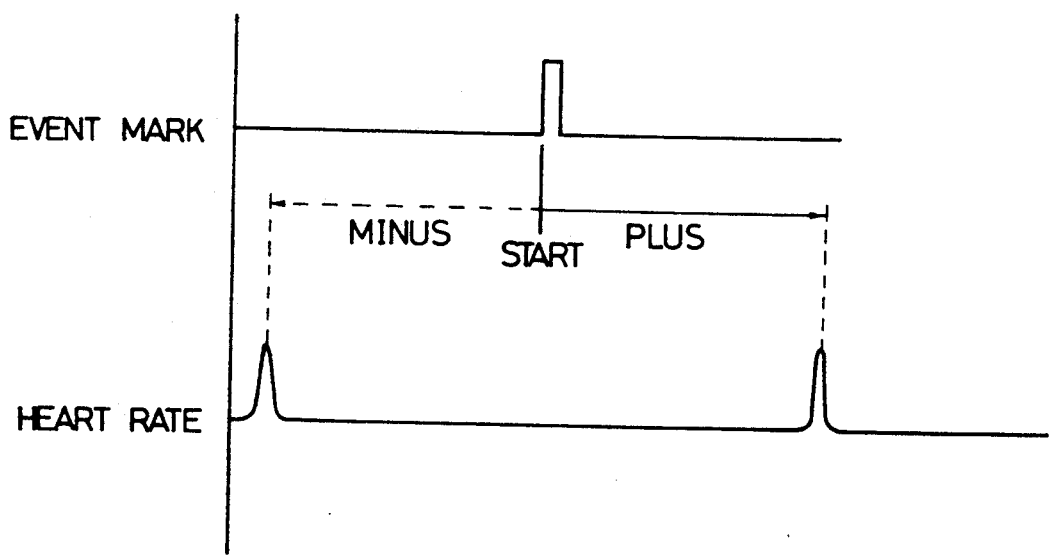

The time difference between the occurrence of even marks and the occurrence of peaks or valleys of the fetal heart rate curve will be obtained in any of the following two methods. Method a (FIG. 10A):

As shown in FIG. 10A, each time the peak or valley of the fetal heart rate curve is detected during the observation, counting of the time starts. The time is counted until an event mark occurs. The time duration between the occurrence of the peak or valley of the curve and the detection of the event mark is set as a "positive" time difference (which is put on the positive side of the axis of the abscissa in FIG. 7), and the time duration between the occurrence of that event mark and the occurrence of a subsequent peak or valley of the heart rate curve is a "negative" time difference (which is put on the negative side of the axis of the abscissa in FIG. 7). Method b (FIG. 10B):

In this method, the occurrence of event marks is being observed, as shown in FIG. 10B. Each time a peak or valley of the fetal heart rate curve occurs, the time duration between the event mark and this peak or valley is calculated. Other parts are the same as those in the method a.

The time differences and the heart beat differences obtained in either of the above-described methods are graphically presented, with the axis of the abscissa representing, for example, the time difference while the axis of the ordinate represents the heart beat difference. The time difference is recorded in a range from plus or minus a few minutes to ten minutes, with the time at which an event mark occurs being an origin. The heart beat difference is recorded in a range from minus several tens of beats per min to plus several tens of beats per min to 70 beats per min, with the mean heart rate being an origin. In this NST graph, in addition to the two-dimensional plotting of the "heart beat differences" with respect to the "time differences", plot points may be recorded in a plurality of ways. More specifically, continuance of the peak of the fetal heart beat for 15 seconds or longer may be represented by, for example, a mark (★), and continuance of the peak for a time duration of less than 15 seconds may be represented by, for example, a mark (◎). Whether or not a fetus is reactive is determined by the occurrence of transient tachycardia (continuance of a heart beat difference of plus 15 BPM or above for 15 seconds or longer). So, the determination can be made easily using the NST graph, if the line indicating the heart beat difference of plus 15 BPM is recorded on the NST graph and if continuance of the peak for 15 seconds or longer and continuance of the peak for a period of less than 15 seconds are shown using two different marks. At that time, the number of times the event marks occur, the number of occurrences of continuance of the peak for 15 seconds or longer, or the number of occurrences of continuance of the peak for not more than 15 seconds may also be shown in the graph to help make the determination.

As shown in FIG. 7, a line (a broken line in the figure) indicating a heart beat difference of plus 15 BPM or above may be drawn on the graph for convenience.

The number of times the event marks occur, the number of cases of continuance of the peak or valley for 15 seconds or longer, or the number of cases of contuance of the peak or valley for not more than 15 seconds may also be shown to increase the usefulness of the graph.

In this way, the operation required to obtain the time difference between the event marks and the peaks of valleys of the fetal heart rate curve and the heart beat difference between the mean heart beat and the peaks and valleys of the heart rate curve can be simplified. Further, the number of times the event marks occur can also be mounted easily, which would be impossible with the conventional apparatus.

Variability or whether a fetus is reactive or non-reactive is determined by a doctor.

Histogram Record

Figure 8:
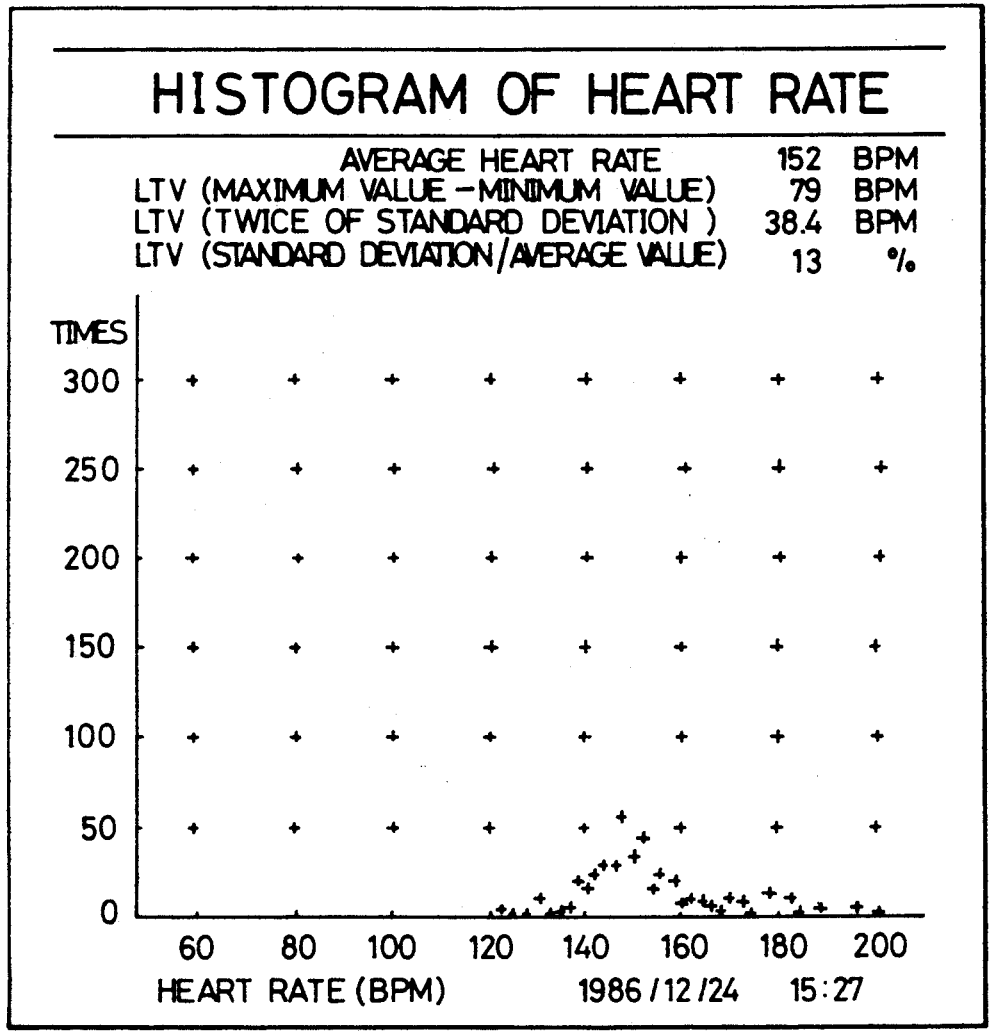
Figure 9:
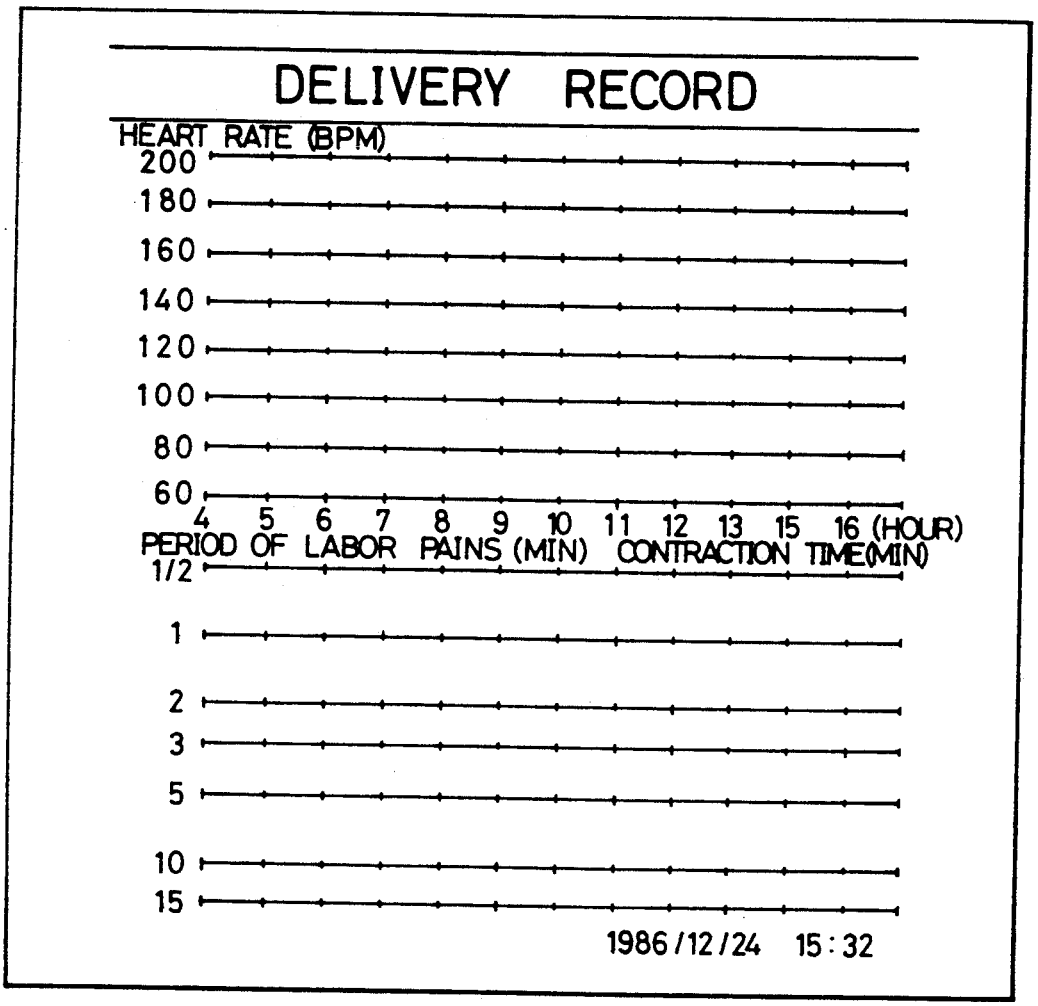

Both the histogram (shown in FIG. 8) and the record (shown in FIG. 9) are obtained by pressing the switches 7 and 9, respectively. FIG. 9 shows an example of a "delivery record" in which the fetal heart rate data, the labor pain period data and the contraction time data for the 12 hours are plotted each 15 minutes. FIG. 8 shows a "histogram" in which the frequency distribution of the fetal heart rate for the 2 to 7 minutes, the average heart rate and LTV's (long term variabilities) are plotted.

In addition to the aforementioned reasons, the following reason necessitates the provision of the histogram and the record. The fetus monitoring apparatus is constantly collecting and recording data on the fetal heart rate, the period of labor pains and the contraction time, and the data obtained by processing the above-described types of data can obviate a task performed by a nurse or the like periodically (parto gram which it a trendgraph in which the fetal heart rate, the period of labor pains, the contraction time and so on are plotted). The recording (printing) technique has undergone improvement recently, and preparation of the histogram and the record is enabled by the provision of a digital recorder, such as a thermal line printer, in which figures and tables, together with curves, can be printed out easily.

In this embodiment, the figures or tables obtained by processing the data are printed out by the thermal line head printer 3.

The delivery record is a graphic representation of, for example, variations in the fetal heart rate during the delivery, the period of labor pains, and the contraction time with time over the past 12 hours.

Fetal Heart Rate:

The arithmetic mean over the past 15 minutes, or the instantaneous value, is obtained every minutes, each 15 minutes, each 30 minutes and each 45 minutes, respectively.

Period of Labor Pains

The value observed over the past 15 minutes is recorded every minutes, each 15 minutes, each 30 minutes and each 45 minutes, respectively.

Time Duration of Contractions

The value observed over the past 15 minutes is recorded every minutes, each 15 minutes, each 30 minutes and each 45 minutes, respectively.

In the histogram, the frequency of the fetal heart rate over the past few minutes, the average heart rate and LTVs are, for example, graphically shown. Regarding the data corresponding to the flat portions of the fetal heart rate in the past few minutes, Frequency: Graphic representation of the above-described data, Average heart rate: Arithmetic mean (TO) of the above-described data LTV (1): Difference between the maximum value and the minimum value (Max−MIN)

(2): Twice the standard deviation ($=2 * \sigma$)

(3): Standard deviation/average value ($=\sigma/TO$)

The LTV represents variations in the fetal heart rate with respect to time, which are the relatively small baseline variations of the fetal heart rate that can be visually recognized.

The delivery record has advantages in that:

(1): The quality of data is improved.

Although only the data in the vicinity of the measurement time (each 60 minutes, 30 minutes or 15 minutes) is employed conventionally, in this embodiment, it is possible to process the overall data obtained between the previous measurement and the present measurement. This eliminates the special data, enabling the recording of more objective data. For example, the heart rate obtained conventionally is the average value of the past 15 seconds or 60 seconds. However, in this embodiment, the average value of the past 15 minutes or 30 minutes is possible. Of course, the average value of the past 15 seconds, which is obtained conventionally, can also be obtained.

(2): Saves labor

Conventionally, measurement of the fetal heart rate is a troublesome task. In particular, measurement every 15 minutes is troublesome. For example, in a case where the period of labor pains in from a few minutes to 10 minutes, the observer cannot be away from the monitoring apparatus, because, even if the chart is read later, confirmation of the time and the reading of the chart are troublesome.

The histogram has advantages in that:

(1): The quality of data is improved

In the present embodiment, average heart rate errors or LTV errors can be eliminated, which would be caused when these values are determined on the basis of the visual observation of the fetal heart rate curve. Conventionally, the results of the determination are varied, depending on the individuals or the angle at which the chart is looked at. Further, the LTVs are pratically obtained intuitively.

In this embodiment, since the fetal heart rate data obtained over the past few minutes is directly processed to obtain the average fetal rate or LTVs, errors resulting from the visual observation of the curve can be eliminated. Alternatively, part of the LTVs can be calculated.

(2): Saves labor

Conventionally, the average heart rate of the LTVs is obtained from the fetal heart rate curve using a scale, or the LTVs are calculated from the fetal heart rate curve. This embodiment eliminates all of these trouble tasks.

Twin Monitoring Function

Figure 11:
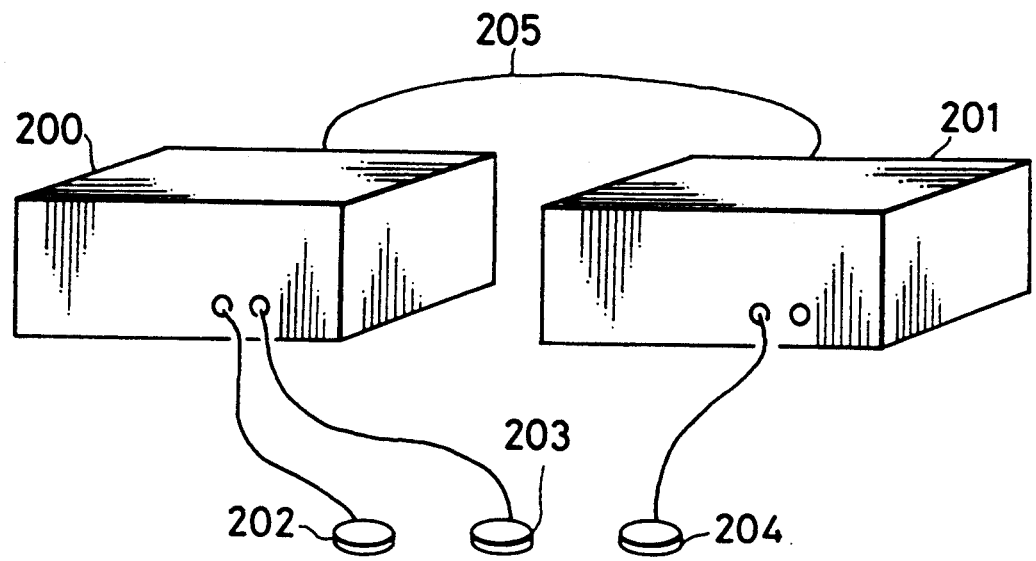
FIG. 11 illustrates how two fetus monitoring apparatuses are connected to each other to monitor a twin.

Monitoring of twins is performed by using two fetus monitoring apparatuses 200 and 201 with the individual Doppler probes employing different frequencies, as shown in FIG. 11. A probe 203 of the fetus monitoring apparatus 200 is provided on the abdomen of a gravida to measure the intensity of labor pains, and a ultrasonic Doppler probe 202 thereof is directed toward the heart of one of the fetuses. Also, the labor pain intensity data (the output of the driver 117g of the apparatus 200) detected by the fetus monitoring apparatus 200 is sent to the other fetus monitoring apparatus 201 through a cable 205. A Doppler probe 204 of the fetus monitoring apparatus 201 is disposed toward the heart of the other fetus, and the labor pain intensity data (received by a receiver 117b of the apparatus 201) sent from the fetus monitoring apparatus 200 is recorded as a labor pain intensity curve. In this way, processing of the labor pain intensity signal in accordance with the fetal heart rate curve of the other fetus can be performed in the fetus monitoring apparatus 201 in which no labor pain intensity signal is detected.

Hence, the fetal heart rate can be monitored in synchronism with the mother labor pain intensity signal for each fetus of the twins, and the delivery record, the histogram, and the NST graph can be output separately for the individual fetuses, which is convenient for diagnosis.

In FIG. 3B, the internal labor pain intensity signal is output to an external fetus monitoring apparatus through the driver circuit 117g, and a fetus monitoring apparatus receives the labor pain intensity signal from the other apparatus through the receiver circuit 117b. These interface terminals are provided on the rear side of the apparatus.

When a twin monitoring system is to be formed by using two fetus monitoring apparatuses, as shown in FIG. 11, the cable 205 is connected to a rear connector (which is in turn connected to the receiver 117b shown in FIG. 3B) of the fetus monitoring apparatus 201. The connector has a protrusion (not shown). When the cable 205 is connected, this protrusion is pressed, by means of which a signal line 200 (FIG. 3B) is established, enabling the multiplexer 130 to select an external labor pain intensity signal.

Figure 21:
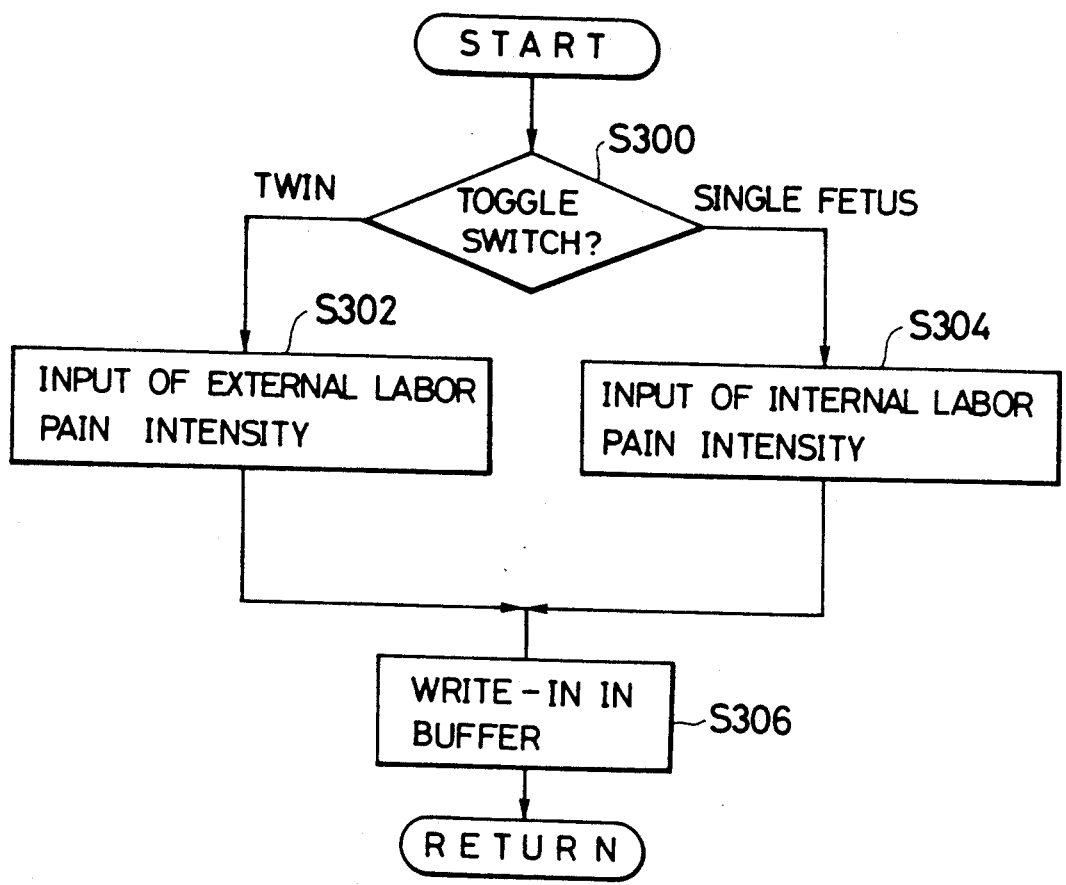

In the above-described method, an input system is mechanically divided by means of the protrusion on the connector. However, it may also be arranged such that a toggle switch (not shown) for indicating "twin" and "single fetus" is provided on the operation panel and such that, when the CPU 100 detects that the toggle switch has been turned to the "twin" side, it allows the multiplexer 130 to select an external labor pain intensity signal. FIG. 21 is a flowchart of the procedures executed by the fetus monitoring apparatus which is used as the fetus monitoring apparatus 201 shown in FIG. 11. As is clear from the flowchart, the CPU 100 of the fetus monitoring apparatus 201 detects the state of the toggle switch, determines the signal to be selected by the multiplexer 130, either the external labor pain intensity signal or the internal labor pain intensity signal, and then stores the signal selected in the buffer within the CPU 100.

Twins occur at a rate of about 1 case per 152 cases. Delivery of twins tend to become abnormal, thereby causing fetal asphyxia or neonatal asphyxia. The use of the conventional fetus monitoring apparatus with the Doppler probe employing a different frequency is therefore uneconomical. Also, it is not easy to use the fetus monitoring apparatus together with an electrocardiograph. Hence, a monitoring system with two fetus monitoring apparatuses is appropriate.

The twin monitoring system in the present embodiment employs two fetus monitoring apparatuses which are capable of monitoring individual fetuses independent of each other.

The fetus monitoring apparatus shown in FIG. 1 can be used as a single unit to monitor a single fetus. It can also be used to form a twin monitoring system, which is achieved by the connection thereof to another fetus monitoring apparatus of the same type. Accordingly, we, the present inventors, propose the following modified example. A second fetus monitoring apparatus of the twin monitoring system may be formed as the one which has no means for inputting an internal labor pain intensity signal (FIG. 5B) and to which a labor pain intensity signal is always supplied externally through the receiver 117b. In this way, cost of the overall twin monitoring apparatus can be decreased.

Alarm Function

Generally, a fetus monitoring apparatus is designed to monitor the fetal heart beats by virtue of Doppler effect. Fetal activity can be observed to some extent by observing the fetal heart beats. Accordingly, in this embodiment, issuance of an alarm of the heart beats is performed using three thresholds, which respectively indicate "normal", "close to anomaly, and "abnormal" states. This "close to anomaly" state is "caution", which is warned in a way different from that in which "abnormal" is warned. In this way, sudden occurrence of "abnormal" state can be avoided, and how "caution" proceeds to "abnormal" can be clarified to some extent. For example, a heart rate of 100 BPM or less or 180 BPM or above may be set as "alarm" state ( which is "abnormal"), with a heart rate from 101 BPM to 119 BPM or from 161 BPM to 179 BPM being "caution" state and a heart rate from 120 BPM to 160 BPM being "normal" state.

In the embodiment shown in FIG. 1A, warning of both "alarm" and "caution" is performed visually by using the alarm display 16 and the caution display 17 and by using sounds which are heard from the speaker 121. More specifically, in "caution" state, the caution display 17 lights up and, at the same time, the speaker 121 produces a cautioning sound. When "abnormal" state occurs, the alarm display 16 lights up, and the speaker 121 makes a sound which differs from that indicating "caution". Since monitoring of the fetal heart beats is very important under a circumstance where warning is issued, "caution" may be warned using actual fetal heart beats which are output at a preset volume. When a fetus is normal, the fetal heart beats are heard at a volume which is set manually (by adjusting the volume adjusting switch 19 provided on the front of the apparatus and the volume 134). When the fetus's condition becomes slightly bad and the heart rate reduces to 119 BPM or below, the speaker makes a sound at a larger volume (at the preset volume in almost all the cases), either the one which is preset (by adjusting the volume 133) or the one which is manually set by adjusting the volume 134. This sound that warns "caution" is not offensive to one's ears but it is rather the information on the fetal activity. When the fetal condition worsens, an alarm sound is generated in a tone that attracts everyone's attention. This two-stage alarm enables the monitoring of the progress of the fetal activity.

The CPU 100 periodically scans the MPX 130 to detect the resistances of the two volumes. Once the larger resistance is determined, the CPU 100 disables the smaller one. Since the volumes 133 and 134 are incorporated within the amplifying circuit 120, the heart beats which have passed through the MPX 118 are amplified at the set volume before being output from the speaker. The MPX 118 selects either the internal heart beat sound which is generated within the apparatus or the external heart beat sound which is sent from another apparatus (through the receiving circuit 117f) in accordance with the instruction from the CPU 100. An alarm sound generating circuit 119 determines whether the state is in "caution, "alarm" or "normal" from the heart rate detected, and generates the sound having a tone corresponding to either "caution" or "alarm" state.

Figure 12:
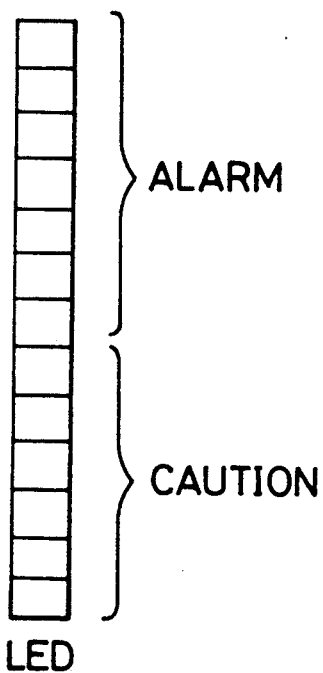
FIG. 12 shows a modified example of alarming.

In another embodiment in which the "alarm" is warned by using fetal heart beats generated at a preset volume, an alarm may also be issued using binary digits. The display portions 16 and 17 (FIGS. 1A and 1B) may also be structured such that LEDs are aligned in a line, as shown in FIG. 12. In that case, the circuit is constructed in the same manner as that of the cases of the components 105, 109, 110 and 111.

External Communication/Interface Function

As stated previously, this embodiment of the fetus monitoring apparatus is capable of transmitting all the signals, including the heart beat signal, the heart beat sound, the labor pain intensity signal and so on, to an external fetus monitoring apparatus. The fetus monitoring apparatus is also capable of receiving the above-described three types of signals from another fetus monitoring apparatus and processing them. The internal heart beat sound is transmitted to an external apparatus through the driver 117d, and the external heart beat sound is received through the receiver 117f. The internal heart beat signal is transmitted through the driver 117a, and the external heart beat signal is received through the receiver 117e. The internal labor pain intensity signal is transmitted through the driver 117g, and the external labor pain intensity signal is received through the receiver 117b.

When a heart beat signal is to be output to an external circuit, the CPU 100 sends the amine data corresponding to the heart rate to a PIT (programmable interval timer) 114 to convert the heart rate into a duty cycle. The resultant duty cycle is converted into an analog signal, and this analog signal is output from the driver 117a.

Data other than the heart beat data and the labor pain intensity data (e.g., data representing the body temperature of a mother, the size of the opening of uterus, the maximal/minimal blood pressures and so on), together with the heart beat and labor pain intensity, are input from the output to an external apparatus (e.g., CRT or the like) through an interface 117c. The interface 117c is a bidirectional receiver/transmitter circuit. Data is fed from the CPU 100 to the interface 117c through a USART (universal asynchronous synchronous receiver transmitter) 116. In this way, the heart beat data or the labor pain intensity data obtained by the fetus monitoring apparatus, together with other data, may be color displayed on a CRT display or the like.

DSP

The DSP (digital signal processor) 103 is the center of the data processing required for the heart beat signal. A heart beat signal is periodic and is buried in noise. In order to obtain a heart rate with a high degree of accuracy from the periodic signal, a large amount of data has to be processed generally. In this embodiment, a heart rate is calculated using the autocorrelation technique. In this embodiment, data is input at a sampling rate of 3 ms at a maximum in accordance with the autocorrelation procedure to achieve a resolution of 0.5 BPM, and data processing is performed on the data corresponding to a past few beats in accordance with the autocorrelation procedure in order to improve accuracy.

Conventionally, execution of data processing by means of this autocorrelation technique requires a device having a size corresponding to at least a minicomputer. This embodiment of the fetus monitoring apparatus employs a digital signal processor TMS 32010 manufactured by Texas Instrument in U.S.A. This enables manufacture of a fetus monitoring apparatus which is small in size and which is capable of processing a large amount of data. FIG. 4 shows the DSP 103 in detail. In the example shown in FIG. 4, the autocorrelation heart rate operation programs are stored in a ROM 142, and intermediate data used in the calculation is stored in SRAMs 140 and 142. The resultant heart rate obtained by the calculation is stored in the common RAM 143, which is a write-only memory from which the heart rate is read out at appropriate intervals by the CPU 100.

Figure 13A:
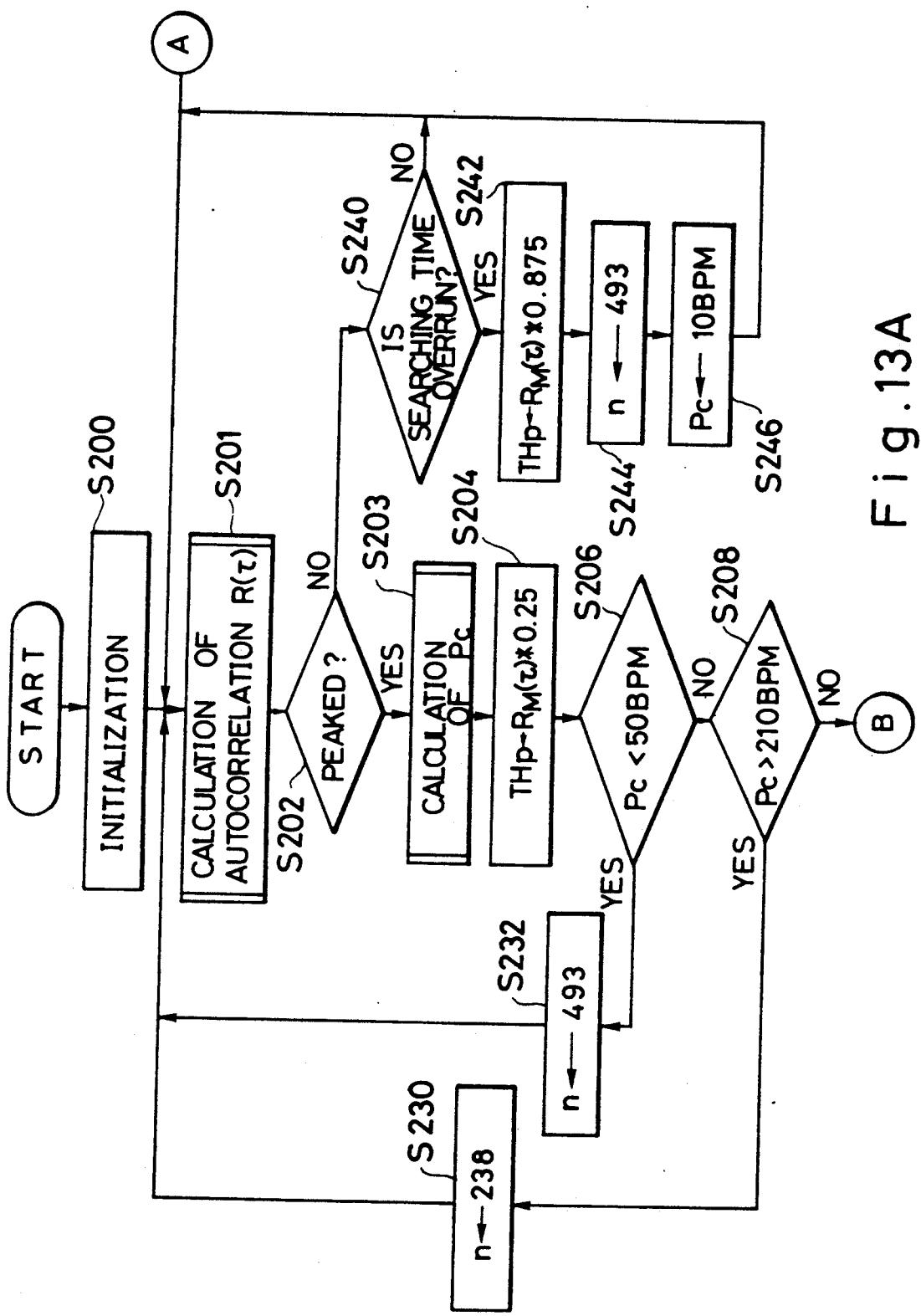
FIGS. 13A, 13B, 14 to 21 are flowcharts of the control procedures employed in the present invention.
Figure 13B:
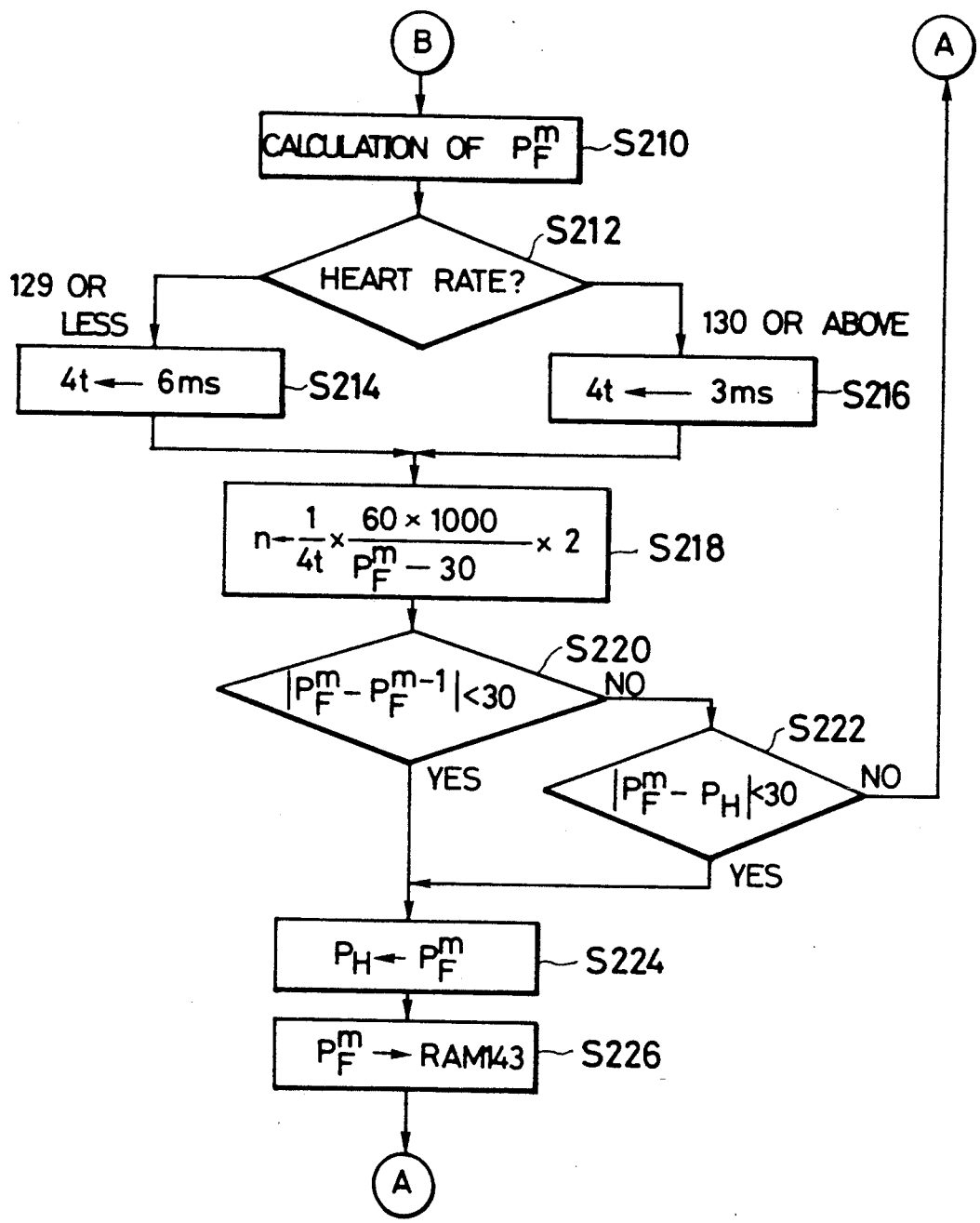

FIGS. 13A and 13B are flowcharts of the control procedures executed by the DSP 103 to operate a heart rate. In the DSP 103, the routine for fetching data from the A/D converter 102 is executed concurrently with the operation routine shown in FIGS. 13A and 13B. However, the data fetching routine is a known one, further description thereof being omitted. In the present embodiment, autocorrelation operation is performed in accordance with the following equation:

$$R(\tau) = \frac{1}{n} \cdot \Sigma f(k \cdot \Delta t) \cdot f(k \cdot \Delta t + \tau)$$

where n is the number of sampled data, $\Delta t$ is the sampling rate, f represents the digital heart beat data from the A/D converter 102, and $K=1$ is the latest data. $\tau$ is integral multiples of $\Delta t$. In this equation, the autocorrelated value of the heart beat signals which are separate from each other by a time interval $\tau$ is calculated.

In the program shown in FIGS. 13A and 13B, the number of sampled data n or the like used to measure a first heart rate after power on is initialized in step S200. Next, in step S201, a correlated value R ($\tau$) is obtained in accordance with the above-described equation. When τ becomes identical with the period of the heart beats, R(τ) is peaked. In the program loop consisting of steps S201, S202, S240 and S201, the peak of the correlated value is therefore searched. This search is performed by comparing the threshold THp determined on the basis of the maximum value $R_M(\tau)$ of the previously calculated correlated values R(τ) with the present R (τ). Once the peak value is obtained, a rough heart rate $P_C$ of the present operation cycle is obtained in step S203. It is to be noted that secondary interpolation is performed on this rough heart rate $P_C$ later in step S210 to obtain an accurate heart rate $P_F^m$.

If it is determined in step S240 that the searching time has been overrun, it is judged that setting of the threshold value THp used to determine the peak value, the number n of sampled data and so on is inadequate. In consequence, in step S242, a value which is 0.875 times the present threshold THP is set as the new threshold THP, that is, $$THp \leftarrow R_M(\tau) \times 0.875,$$

in step S244, the maximum value, 493' is set as the number n of sampled data, and then in step S246, 10 BPM is set as the rough heart beat $P_C$.

Once the peak value has been found in step S202 and the rough heart rate PC has been obtained, threshold THp is replaced with a new value in step S204 as follows:

$$THp \leftarrow R_M(\tau) \times 0.25$$

Next, in steps S208 and S210, it is determined whether or not the rough heart beat PC is less than 50 BPM or exceeds 210 BPM. When setting of the number n of sampled data is not appropriate, $P_C$ becomes less than 50 BPM or exceeds 210 BPM. In consequence, if $P_C$ is less than 50 BPM, 493 (6 ms×493=2958 ms) is set to n. If PC exceeds 210 BPM, 238 is set to n (which is equal to 714 ms=3 ms×238) in step S232.

When $50 < P_C < 210$, secondary interpolation of the autocorrelation is performed on the rough heart rate to obtain an accurate heart rate $P_F^m$ (where m indicates that this is the present value) in step S210. Secondary interpolation is performed for the purpose of obtaining an accurate high heart rate. Generally, secondary interpolation provides for a value which is four or five times more detailed than the value which is obtained without secondary interpolation. In order to obtain an accurate high heart beat, e.g., in order to ensure, for example, 0.5% or less of errors, occurrence of errors has to be within 1 BPM when the heart rate is 200 BPM, which means that a resolution of about 0.5 BPM is required. This also means that the difference (which is 0.75 ms) between 200 BPM=300 ms and 200.5 BPM=299.25 ms has to be discriminated. In this embodiment, in the case of the sampling time interval Δt of 3 ms, a resolution of 0.75 ms can be obtained by means of the secondary interpolation.

Thereafter, in step S212, it is determined whether the thus obtained heart rate $P_{Fm}$ is 129 or less, or 130 or above. If $P_{Fm}$ is 129 or less, 6 ms is set as the sampling time interval Δt. If $P_{Fm}$ is 130 or above, 3 ms is set as the time interval Δt. This is because, when the heart rate is low, a relatively rough sampling rate Δt ensures the above-described accuracy of 1%. A sampling time interval of 3 ms at 200 BPM and a sampling time interval of 6 ms at 100 BPM ensures the same degree of accuracy.

Next, in step S218, the number n of sampled data for use in a subsequent heart rate operation is determined from the present heart rate $P_F^m$. The present inventors conducted experiments and found that it is preferable for the number n of samples for the subsequent operation to be set between 1.5 beats and 3.5 beats. In practice, an accurate heart rate can be obtained from the data representing two beats in the case of $|P_F^m - 30|$ BPM. More specifically, the number n of samples to be used in the subsequent operation cycle is obtained on the basis of the heart rate $P_F^m$ obtained in the present operation cycle using the following equation:

$$n = \frac{1}{\Delta t} \times \frac{60 \times 1000}{|P_F^m - 30|} \times 2$$

In consequence, in the subsequent operation cycle, autocorrelation and operation of the heart rate are performed using the amount (ms) of data corresponding to the value obtained in the above-described manner. Although the number n of samples for a subsequent operation cycle differs in response to the sampling rates Δt determined in steps S214 and S216, respectively, the minimum value thereof is set to 238 and the maximum value is set to 493. Thus, autocorrelation operation is performed on the amount of data corresponding to a substantially fixed number of heart beats in the overall heat rate area, and this enables calculation of the noise-resistant, balanced heart rate in the overall heart rate area.

Next, in step S220, it is determined whether or not the heart rate $P_F^m$ obtained in the present operation cycle is within ±30 BPM obtained in the previous operation cycle. More specifically, it is determined whether or not $$|P_F^m - P_F^{m-1}| \leq 30$$

Generally, in the operation cycle employed in the present embodiment, the heart rate does not increase or decrease by 30 BPM in one operation cycle. Hence, when the above-described equation is satisfied, it can be considered that the present heart rate $P_F^m$ is reliable, this $P_F^m$ being held as $P_H$ in step S224. Thereafter, in step S226, the present heart rate $P_F^m$ is written in the common RAM 143. Holding of $P_H$ is performed so that $P_H$ can be used to determine which is not reliable, $P_F^m$ or $P_F^{m-1}$, when it is determined in step S220 that $|P_F^m - P_F^{m-1}| > 30$ in a cycle subsequent to the subsequent operation cycle.

If it is determined in step S220 in a certain operation cycle that $P_F^m$ obtained in the present cycle is not reliable, this $P_F^m$ is compared with the held value $P_H$ in step S222. If $P_F^m$ is within 30 BPM of $P_H$, in other words, $$|P_F^m - P_H| > 30$$

it is determined that $P_F^{m-1}$ obtained in the previous cycle is not reliable and that the present $P_F^m$ is reliable. In consequence, $P_H$ is updated in step S224, and $P_F^m$ is written in the RAM 143. Thus, $P_F^m$ is utilized as much as possible so that occurrence of a blank of heart rate data stored in the common RAM 143 can be eliminated. If it is determined in step S222 that $$|P_F^m - P_H| > 30,$$

the processing returns to step S201. By the time the processing of step S201 is executed again, a new heart beat signal has been input to the DSP 103 through the A/D converter 102, enabling the operation of an accurate heart beat to be performed on the basis of this new data..

Assume that $P_F^m$ changes as 150 BPM→150 BPM→150 BPM→190 BPM→150 BPM→150 BPM. The time $P_F^m$ is 190 BPM, $P_F^{m-1}$ is 150 BPM. In consequence, the processing proceeds to step S222. At that time, since $P_H$ is also 150 BPM, the processing returns to step S201. Thereafter, if 150 BPM is obtained as $P_F^m$ in a subsequent cycle, since $P_F^{m-1}$ is 190 BPM, the processing goes to step S222. However, $P_H$ is still 150 BPM, and the processing therefore goes to step S224 then S226 where 150 BPM is stored in the RAM 143 as the heart rate. In other words, in this example, 190 BPM is rejected as noise.

Thus, the heart rate data is calculated by the DSP 103 independent of the CPU 100, the resultant data being stored in the common RAM 143. Because of this provision of the microprocessor DSP 103 dedicated for the heart rate operation, the CPU 100 is capable of concentrating on the processing of the statistical data required for the NST graph, the delivery record and so on. As a result, the heart rate operation and data processing can be performed at the same time, which would be impossible in the conventional single microprocessor from the viewpoint of the speed. Also, the overall size of the apparatus can be reduced.

Control Procedures by CPU 100

FIGS. 14 to 20 are flowcharts of the control procedures which are executed by the CPU 100 (microprocessor 68B09) to provide the histogram, the NST graph, the record and so on.

Figure 14:
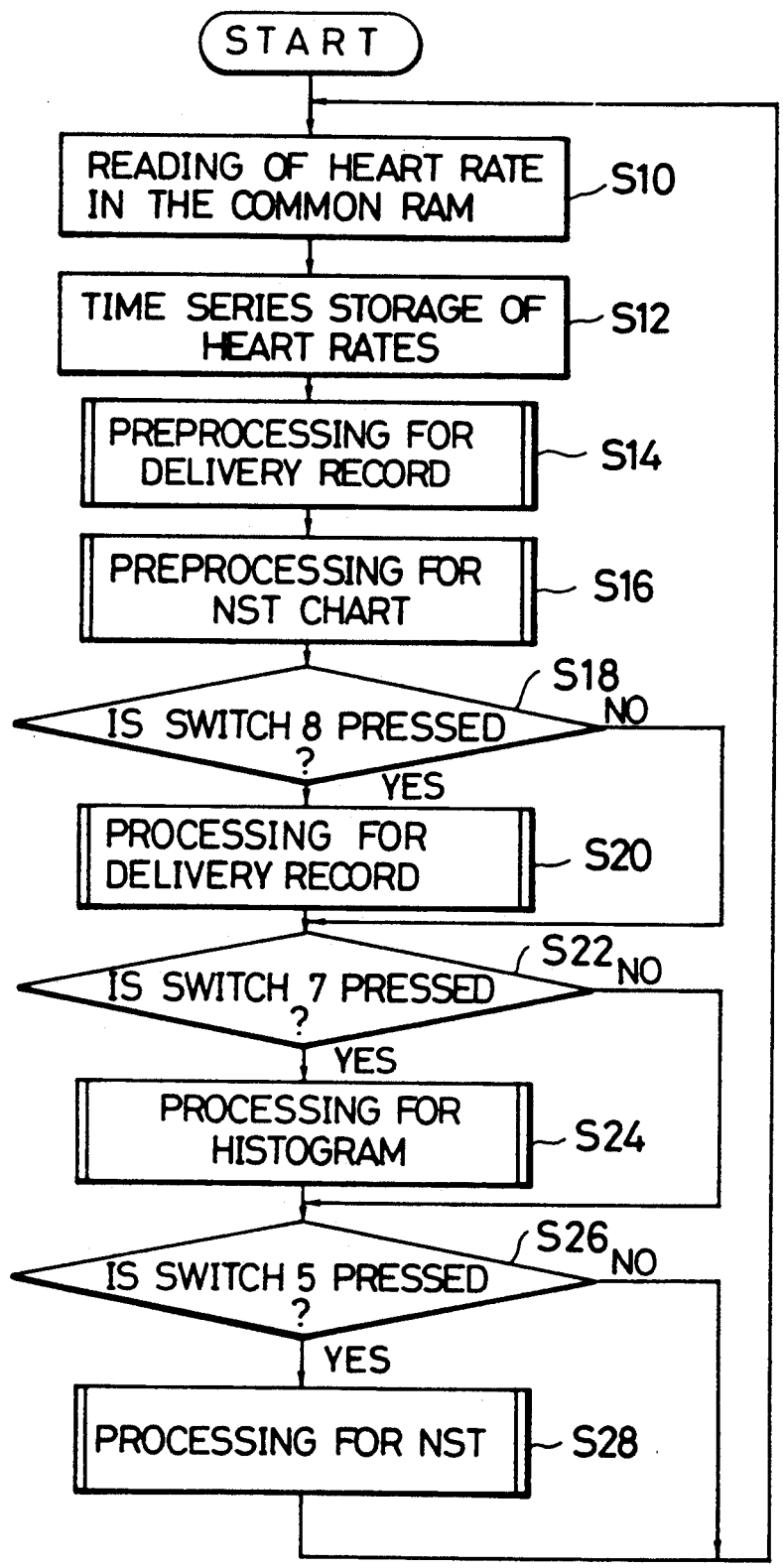

FIG. 14 is a flowchart of the main routine executed to output the histogram, the NST graph, the record and so on on the heart rate data, the labor pain intensity data and so on, which are stored in the buffer within the CPU 100 in time-series (in step S12), in response to the pressing of the corresponding switches (in steps S18, 22, 26). The subroutines executed in step S14 and so on are shown in FIGS. 15 to 20.

Preprocessing for Delivery Record

Figure 15:
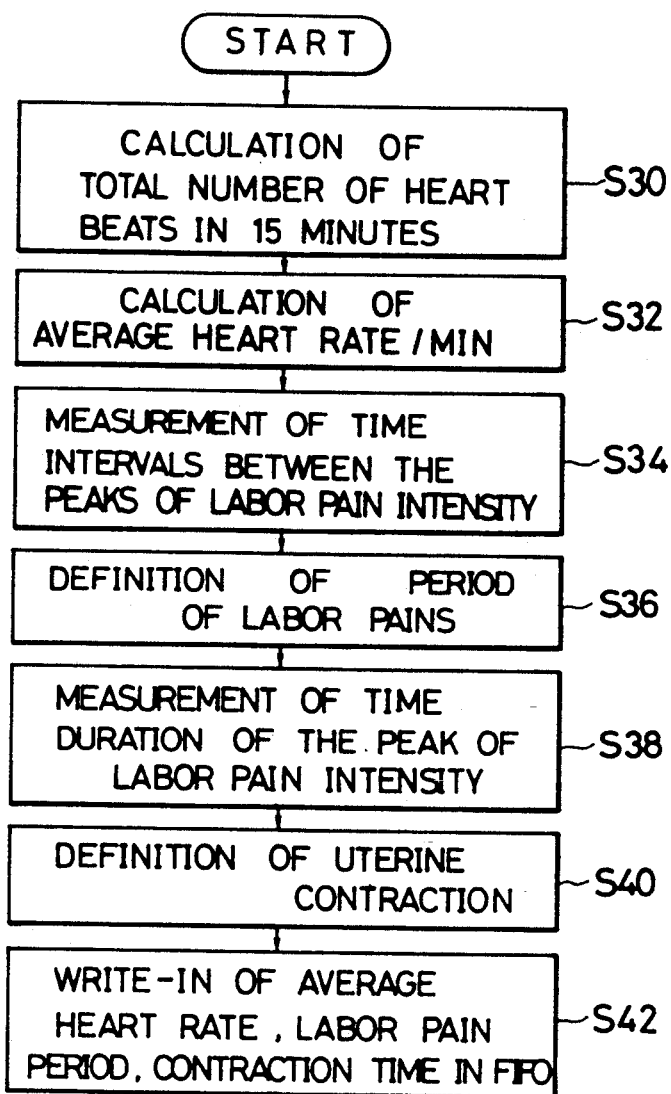
Figure 16:
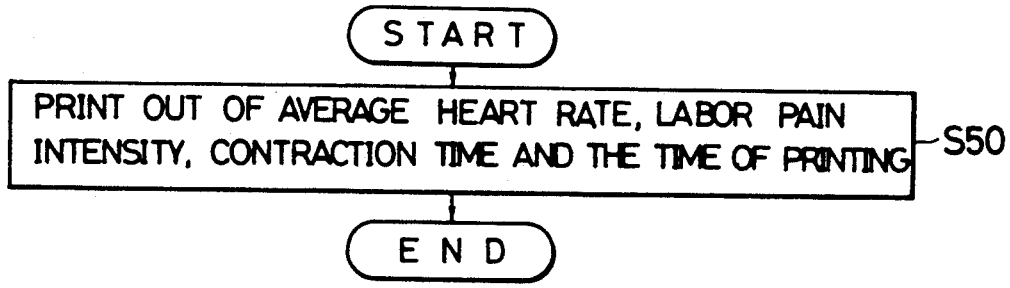

In the processing shown in FIG. 15, the total number of heart beats in 15 minutes is calculated in step S30. Next, in step S32, the average heart rate per minute is calculated from the total number of heart beats in 15 minutes. In step S34, the time interval between the peaks of the labor pain intensity signal is calculated. In step S36, the period of labor pains at that time is defined by selecting the time duration closest to the time interval (the period of labor pains) obtained in Step S34 from among 0 minute, 15 minutes, 30 minutes and 45 minutes. Next, in step S38, the width of the labor pain intensity signal at the time position at which the labor pain intensity signal is peaked is obtained. In step S40, the uterine contraction time is defined by selecting the time duration closest to the time width obtained in step S38 in the same manner as that of the case of the processing in step S36. In step S42, the average heart rate and so on obtained in the above-described processings are stored in the FIFO 122 having a capacity corresponding to 12 hours, thereby completing the preprocessing for the delivery record. In the main routine shown in FIG. 14, each time the heart rate is obtained, this preprocessing is performed, and the resultant data is written in the FIFO 122. As a result, upon pressing of the switch 8, the average heart rate, the period of labor pains, the uterine contraction time and so on for the past 12 hours are output on a sheet of recording paper by the printer 3.

Figure 17:
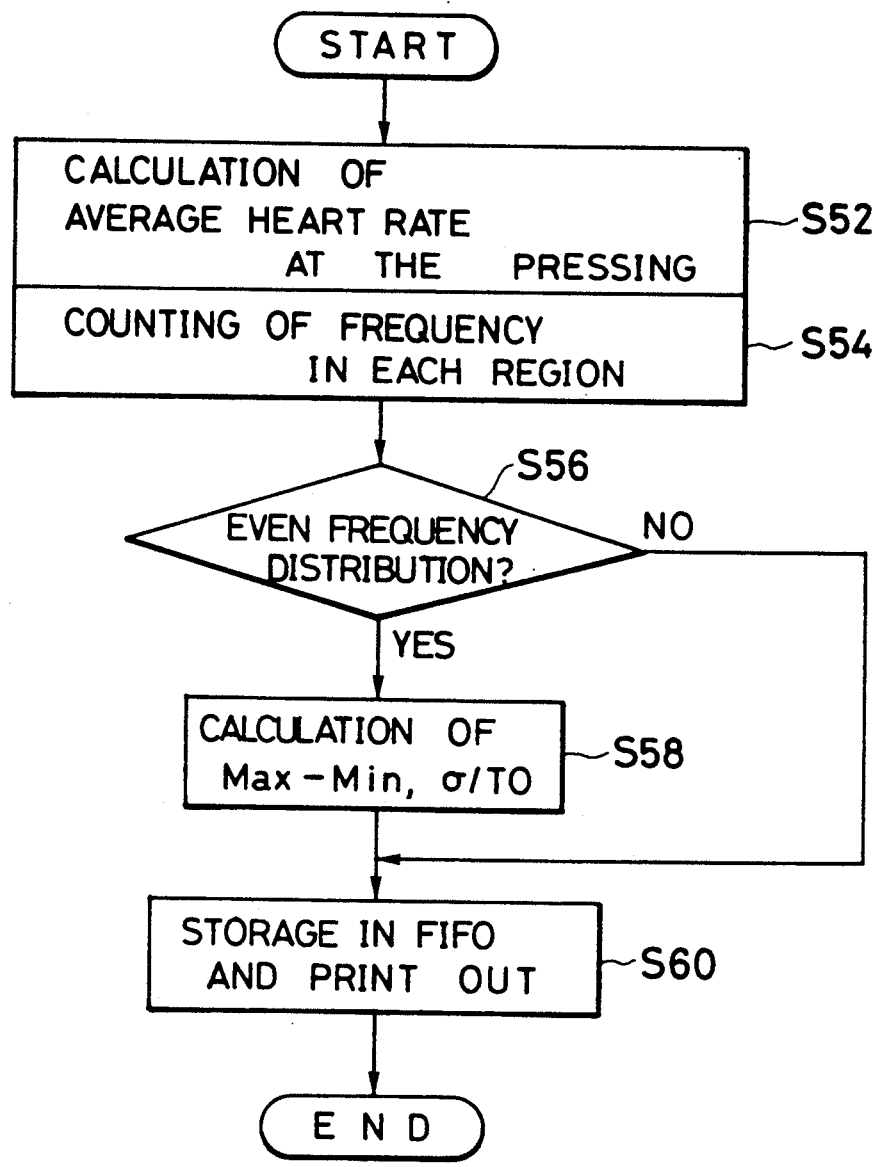

Processing of Histogram (FIG. 17)

Upon pressing of the switch 7, the average heart rate (TO) per minute at the time when the switch 7 is pressed is obtained in step S52. This is the average value of the heart rate of the past 1 to 5 minutes. Next, in step S54, frequency is obtained on all of the heart rate data obtained in the past few minutes (e.g., in the past 5 minutes) for each category of, for example, 2 BPM in the range from 50 BPM to 210 BPM. In step S56, frequency distribution is determined. This determination of the frequency distribution is performed for the purpose of eliminating invalid data, which is necessary to obtain standard deviation or the like. If the distribution is even, the difference between the maximum value and the minimum value, the twice of the standard deviation ($2\sigma$), the value obtained by dividing the standard deviation by the average value ($\sigma/T$) and so on are obtained in step S56. In that case, noise processing is performed on the category of low frequency. In step S58, the thus-obtained value is output to the FIFO 122 for printing.

Processing for NST Graph

Figure 18:
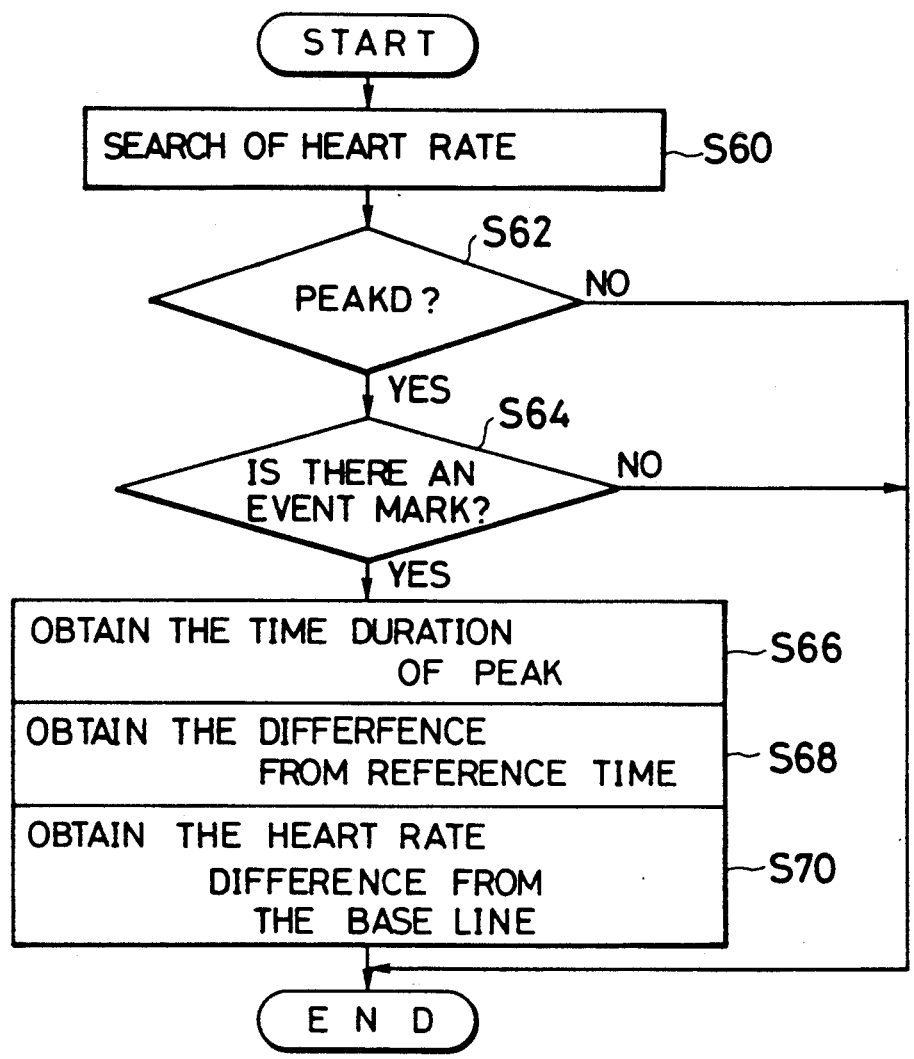
Figure 19:
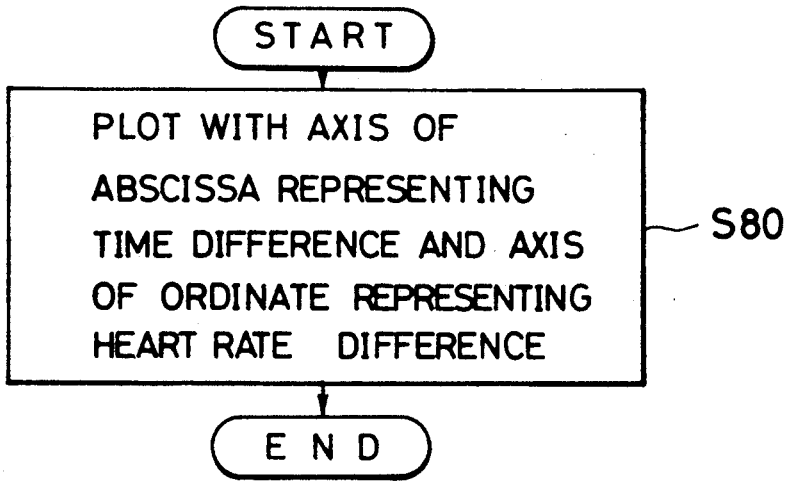

FIG. 18 is a flowchart of the preprocessing performed to obtain the NST graph by the aforementioned method a. In step S60, the heart rates stored in the buffer in the CPU 100 is searched in sequence to detect a peak. Once the peak is detected in step S62, it is determined whether or not there exists an event mark before and after this peak.

If there exists an event mark, the time width of the peak signal is obtained in step S66. Next, in step S68, the time difference from the peak which is the standard time to the detected event mark is calculated. In that case, the time difference from the peak to the event mark which appears after the peak is indicated by a positive 0 value, and the time difference from the peak to the event mark which occurred before the peak is represented by a negative value. Next, in step S70, the heart rate difference from the standard heart rate (the base line) to the peak (or the valley) is calculated.

Execution of the processings from step S60 to step S70 is repeated on the main routine until the switch 7 is pressed so as to successively calculate the time difference and the heart rate difference.

Once the switch 5 has been pressed, the processing goes from the main routine to step S80, and the obtained data is printed out as the NST graph in which the axis of abscissa represents the time difference and the axis of ordinate represents the heart rate difference. At that time, various types of data shown in FIG. 7 are also printed out in addition to the two dimensional graphic illustration.

Figure 20:
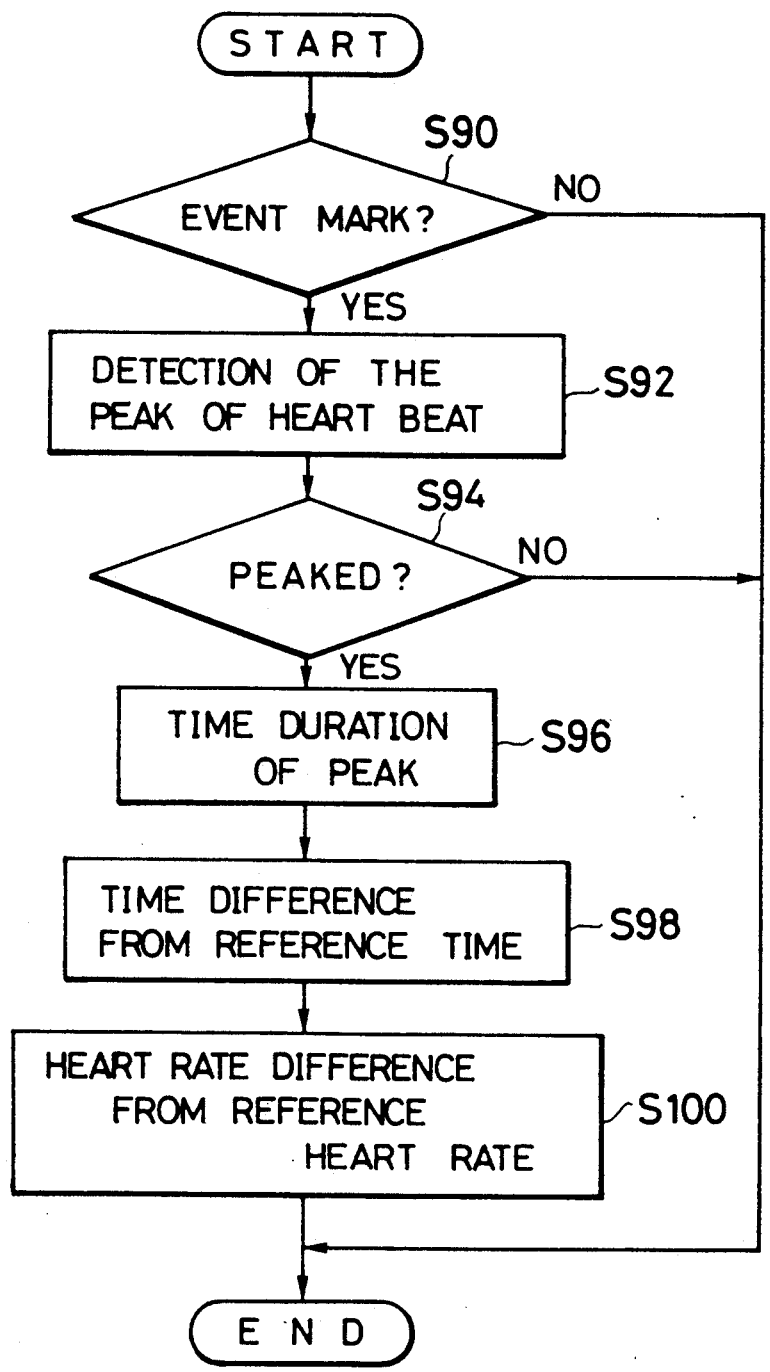

FIG. 20 is a flowchart of the preprocessing which is performed using the aforementioned method b to output the NST graph. This flowchart differs from the one shown in FIG. 18 in that occurrence of an event mark is searched for to provide the standard time and in that the time difference from this standard time to the peak of the heart beat is then obtained. In the flowchart of the preprocessing performed by the method b, the time difference is represented by a value of an inverted sign.

The fetus monitoring apparatus shown in FIG. 1 is of the type which employs the algorithm in which the time difference is calculated by the method a. However, the fetus monitoring apparatus may also be arranged such that it employs the algorithms according to the methods a and b. In that case, the apparatus is provided with two types of switches 5, and the algorithms are switched over by the pressing of the corresponding type of switch 5.

What is claimed is:

1. A fetus monitoring apparatus comprising:

a memory means for time orderly storing fetal pulse signals representative of a fetal continuous state and mother pulse signals representative of the continuous state of a mother;

time difference calculation means for calculating a difference between a time when a fetal pulse signal is present and a time when a mother pulse signal is present stored in said memory means, a time difference calculation being made each time either one of the fetal pulse signal and mother pulse signal stored is present;

pulse rate calculation means for calculating pulse rates of either one of the fetal and mother pulse signals stored in the memory means, each time when said time difference calculation means calculates the time difference; and outputting means for correlatively and two-dimensionally outputting a visual output in a manner that the pulse rates calculated by the pulse rate calculation means is on one axis of the two-dimensional visual output, and the time differences calculated by the time difference calculation means are on another axis of the two-dimensional visual output.

2. The fetus monitoring apparatus of claim 1, wherein said fetal pulse signal comprises a Doppler heart beat signal.

3. The fetus monitoring apparatus of claim 1, wherein said mother pulse signal comprises a labor pain intensity signal.

4. The fetus monitoring apparatus of claim 1, wherein said fetal pulse signal comprises a Doppler heart beat signal and said mother pulse signal comprises at least an event mark signal.

5. The fetus monitoring apparatus of claim 4, wherein said pulse rate calculation means includes means for calculating a heart beat from said Doppler heart beat signal, and wherein said correlation is represented by a time difference between an occurrence of a peak of said heart beat and an occurrence of said event mark signal, and a heart beat value difference between the heart beat value at said peak and a heart beat value at the occurrence of said event mark signal.

* * * * *

UNITED STATES PATENT AND TRADEMARK OFFICE
CERTIFICATE OF CORRECTION

PATENT NO.   :   5,069,218
DATED        :   December 3, 1991
INVENTOR(S)  :   Makoto IKEDA It is certified that error appears in the above-identified patent and that said Letters Patent is hereby corrected as shown below:

Title page, Section [56] References Cited, right column, insert after "Foreign Patent Documents", the following:

OTHER DOCUMENTS

Brochure for Fetal Monitor, Model 115, Corometrics Medical Systems, Inc., April 1984.

Brochure for Models 8040A and 80300A, Cardiotocograph, Hewelett Packard Company. (Believed published in 1985 or earlier.)

Column 17, line 63, change "amine" to read --time--.

Column 22, line 43, delete "0" after "positive".

Title page, Abstract, line 3, insert --beat-- after "heart".

Signed and Sealed this

First Day of June, 1993

Attest:

MICHAEL K. KIRK

*Attesting Officer*  *Acting Commissioner of Patents and Trademarks*